A

United States Patent [19]

Devare et al.

[11] Patent Number: 6,153,377
[45] Date of Patent: *Nov. 28, 2000

[54] SYNTHETIC DNA DERIVED RECOMBINANT HIV ANTIGENS

[75] Inventors: Sushil G. Devare, Northbrook; James M. Casey, Gurnee; Suresh M. Desai, Libertyville, all of Ill.

[73] Assignee: Abbott Laboratories, Abbott Park, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/443,961

[22] Filed: May 18, 1995

Related U.S. Application Data

[62] Division of application No. 08/314,570, Sep. 29, 1994, Pat. No. 5,859,193, which is a continuation of application No. 08/066,610, May 24, 1993, abandoned, which is a continuation of application No. 07/895,187, Jun. 5, 1992, abandoned, which is a continuation of application No. 07/275,309, Nov. 23, 1988, abandoned.

[51] Int. Cl.[7] ........................................ C12Q 1/70
[52] U.S. Cl. .............................. 435/5; 435/7.1; 435/69.1; 435/69.3; 424/188.1
[58] Field of Search .................................. 435/7.1, 71.1, 435/172.3; 424/188.1, 208.1

[56] References Cited

U.S. PATENT DOCUMENTS

| | | |
|---|---|---|
| 4,753,873 | 6/1988 | Beltz et al. . |
| 4,861,707 | 8/1989 | Ivanoff et al. . |
| 4,939,094 | 7/1990 | Kuga et al. . |
| 5,079,342 | 1/1992 | Alizon et al. ........................... 530/324 |
| 5,124,255 | 6/1992 | Bolling et al. . |
| 5,156,949 | 10/1992 | Luciw et al. . |

FOREIGN PATENT DOCUMENTS

| | | |
|---|---|---|
| 0001931 | 5/1979 | European Pat. Off. . |
| 0187041 | 7/1986 | European Pat. Off. . |
| 0199301 | 10/1986 | European Pat. Off. . |
| 0331961 | 9/1989 | European Pat. Off. . |
| 0400245 | 12/1990 | European Pat. Off. . |
| WO8803562 | 5/1988 | WIPO . |
| WO8805440 | 7/1988 | WIPO . |

OTHER PUBLICATIONS

Yourno et al., 1988, AIDS Res. Human Retro. 4:165–173.
Srinivasan et al., 1987, Gene 52:71–82.
Gouy et al., 1982, Nuc. Acids Res. 10:7055–7074.
Strongin, W., 1993, "Sensitivity, Specificity, and Predictive Value of Diagnostic Tests: Definitions and Clinical Applications", in Laboratory Diagnosis of Viral Infections, Lennette, E., ed., Marcel Dekker, Inc., New York, pp. 211–219.
Hofbauer et al., 1988, J. Clin. Microbiol. 26:116–120.
Guyader et al., 1987, Nature 326:662–669.
Guyader, M. et al., "Genome organization and transactivation of the human immunodeficiency virus type 2" vol. 326, No. 6114, Apr. 16, 1987, London GB.
Kelley, K.A., et al., "Synthesis of fusion and mature murine alpha interferons in *Escherichia coli*" vol. 45, No. 3, 1986 Amsterdam NL, pp. 317–325.
Desai, et al., "Molecular Cloning and Primary Nucleotide . . . " PNAS, 83: 8380–8384.
Weiss, et al., 1986, "Varialle and Conserved . . . " *Nature*, 324: 572–575.
Alizon et al., 1986, "Genetic Variability of the Aids . . . " *Cell* 46:63–74.
Ratner et al., 1985, "Complete Nucleotide Sequence of the Aids . . . " *Nature*, vol. 313:277–284.
Chang et al., 1985, "Expression in *E coli* of Open Reading Frame Gene Segmends . . . " *Science*, 228:93–96.
Baker et al., 1984, A Gene Regulating the Heat Shock Response . . . USA, 81:6779–6783.
Goldman et al., 1986, "Primary Sequence of . . . ", *Journal of Biological Chemistry*, vol. 261(34):15831–15835.

*Primary Examiner*—Laurie Scheiner
*Assistant Examiner*—Jeffrey S. Parkin
*Attorney, Agent, or Firm*—Priscilla E. Porembski; Andreas M. Danckers

[57] ABSTRACT

The present invention provides a method of synthesizing genes encoding unique HIV-1 and HIV-2 envelope proteins and their fragments, thereby allowing overexpression of these proteins in *E. coli*. The HIV envelope proteins and their fragments have been expressed at high levels as individual proteins or in fusion with other proteins. The HIV envelope proteins thus expressed in *E. coli* can be effectively used for the detection of exposure to HIV as well as the discrimination of HIV-1 and HIV-2.

3 Claims, 32 Drawing Sheets

FIG. 1

```
2. CDC42FRAG.PEP  (1-107)
3. BH102FRAG.PEP  (1-107)
4. SF2FRAG.PEP    (1-107)
1. MALFRAG.PEP    (1-107)
5. SYNFRAG.PEP    (1-107)

2  1 KAQQHLLQLTVWGIKQLQARILAVERYLKDQQLLGFWGCSGKLICTTAVPWNASWSNKtLdQIWNNMT
3  1 EAQQHLLQLTVWGIKQLQARILAVERYLKDQQLLGIWGCSGKLICTTAVPWNASWSNKSLEQIWNNMT
4  1 EAQQHLLQLTVWGIKQLQARVLAVERYLrDQQLLGIWGCSGKLICTTAVPWNASWSNKSLEDIWdNMT
1  1 EAQQHLLQLTVWGIKQLQARVLAVERYLqDQrLLGmWGCSGKhICTTfVPWNsSWSNrSLdDIWnNMT
5  1 KAQQHLLQLTVWGIKQLQARVLAVERYLKDQQLLGIWGCSGKLICTTAVPWNASWSNKSLEDIWNNMT 2 69 WMEWDREIdNYThLIytLIEESQNQQEKNqQELLqLDKW
3 69 WMEWDREInNYTsLIhsLIEESQNQQEKNEQELLELDKW
4 69 WMQWEREIdNYTntIYtLIEESQNQQEKNEQELLELDKW
1 69 WMQWEkEIsNYTgiIYnLiEESQiQQEKNEkELLELDKW
5 69 WMQWEREINNYTNLIYSLLEESQNQQEKNEQELLQLDKW
```

```
                    SmaI
           EcoRI    AvaI  BamHI
1   GAATTCGAGCTCGGTACCCGGGGATCCCATGatgcgcgacaactggcgctctgaactgtacaaatacaa   69
    AsnSerSerValProGlyAspProMETMETArgAspAsnTrpArgSerGluLeuTyrLysTyrLy
               2                   18    23
                                      20
                                                        c-term gp120
70  agttgttaaaatcgaacgctgggcatcgccgaccaaagctaaacgccgttgttcagcgcgaaaa        138
    sValValLysIleGluProLeuGlyIleAlaProThrLysAlaLysArgArgValValGlnArgGluLy
           BglII
139 acgcgcaGATCTAgctgttggtatcctggtgtctctggttttctggtgctgcggttctac           207
    sArgAlaAspLeuValValGlyIleLeuGlyAlaLeuPheLeuGlyAlaAlaGlySerTh
           146
                                          415
208 tatgggctcgctctgactgttcaggctcgccagctgctgtctcgtatcgttcagcagca            276
    rMETGlyAlaArgSerLeuThrValGlnAlaArgGlnLeuLeuSerGlyIleValGlnGlnGl
                                          BamHI
277 gaacaacctgctgcgcgctatcAAGGATcccaaagctcagcagcatctgctgcaactgctgggg        345
    nAsnAsnLeuLeuArgAlaIleLysAspProLysAlaGlnGlnHisLeuLeuGlnLeuLeuGly
                                         302
                           BS2-10
346 tatcaaacaactgcaggctcgcgttctggctgttgaacgctacctgaaagaccagcagctggtat      414
    yIleLysGlnLeuGlnAlaArgValLeuAlaValGluArgTyrLeuLysAspGlnGlnLeuValI
```

FIG. 3A

```
                                                                          EcoRV
829  aggtatcgatgaagaaggtggtgaacgcgaccgcgacctgcctctactcgcctggtagatatctctggc  897
     uGlyIleAspGluGluGluValGluGlyGlyGluValAspArgSerThrArgLeuValAspIleSerLeuAl
                                                                            887
                          413-3
898  tctggtttgggaagacctgcgctctctgtgtttcttaccatcgcctgcgcgacctgctgctgatt  966
     aLeuValTrpGluAspLeuArgSerLeuPheSerCysLeuArgSerTyrHisArgLeuArgAspLeuLeuIl 967  cgctactcgcatcgtgttgaactgctggtgtcgcgcggttgggaagtgctgaaatactgGtgaacctgct 1035
     eAlaThrArgIleValGluLeuLeuValGluLeuGlyArgArgGlyTrpGluValLeuLeuLysTyrTrpTrpAsnLeuLe
               SnaBI
                          413-4
1036 gcaatacgtatctcaggaactgaaaaactgaaaactgtgttttctctggttaatgctactgctgttgc 1104
     uGlnTyrValSerGlnGluLeuLysAsnSerAlaValSerLeuValAlaThrAlaIleAlaValAl
     1043

1105 tgaaggtactgaccgcgttatcgaagttgttcagcgcgcttaccgcgctatcgcgcatatccgccg 1173
     aGluGlyThrAspArgValIleGluValValGlnArgAlaTyrArgAlaIleArgHisIleHisArgAr
                                                  AvaI        HindIII
1174 catccgccaggGtctggaacgcatcctgctgCAGGTGCATGCCTCGAGTCTAGAAAGCTT 1233
     gIleArgGlnGlyLeuGluArgIleLeuLeuGlnValHisAlaSerSerLeuGluSer
                                    1217                 1229
```

FIG. 3C

```
Amino Alphabet      = Identity
Output line length  = 80
Compress            = Off
Randomization       = Off AMINO-Res-length    = 2
DELetion-weight     = 1.00
LEngth-factor       = 0
Matching-weight     = 1.00
NUCLEIC-Res-length  = 4
SPread-factor       = 50

9. MAL      (1-384)
10. ELI      (1-383)
13. Z6       (1-383)
 4. CDC42    (1-384)
12. RF       (1-384)
11. WMJ22    (1-384)
 7. BH8      (1-383)
 8. PV22     (1-383)
 2. BRU      (1-383)
 1. HXB2     (1-383)
 6. BH102    (1-383)
14. HXB3     (1-384)
 3. SF2      (1-384)
 5. SYNGENE  (1-413)
```

FIG. 4A

| | | |
|---|---|---|
| 9 | 1 | MRDNWiSELYKYKVVrIEPLGVAPTKAKRRVVEREKRA IGLGAMFLGFLGAAGSTMGA |
| 10 | 1 | MRDNWRSELYKYKVVVIEPLGVAPTrAKRRVVEREKRA IGLGAMFLGFLGAAGSTMGA |
| 13 | 1 | MRDNWRSELYKYKVVVqIEPLGVAPTrAKRRVVEREKRA IGLGAMFLGFLGAAGSTMGA |
| 4 | 1 | MRDNWRSELYKYKVVVKIEPLGVAPTKAKRRVVQREKRA mLGAMFLGFLGAAGSTMGA VG |
| 12 | 1 | MRDNWRSELYKYKVVVKIEPLGVAPTrAKRRVVQREKRA GAMFLGFLGAAGSTMGA VGTI |
| 11 | 1 | MRDNWRSELYKYKVVVRIEPLGVAPTKAKRRVVQREKRA GAMFLGFLGAAGSTMGA VGTI |
| 7 | 1 | MRDNWRSELYKYKVVVKIEPLGVAPTKAKRRVVQREKRA GALFLGFLGAAGSTMGA VG |
| 8 | 1 | MRDNWRSELYKYKVVVKIEPLGVAPTKAKRRVVQREKRA GALFLGFLGAAGSTMGA VG |
| 2 | 1 | MRDNWRSELYKYKVVVKIEPLGVAPTKAKRRVVQREKRA GALFLGFLGAAGSTMGA VG |
| 1 | 1 | MRDNWRSELYKYKVVVKIEPLGVAPTKAKRRVVQREKRA GALFLGFLGAAGSTMGA VG |
| 6 | 1 | MRDNWRSELYKYKVVVKIEPLGVAPTKAKRRVVQREKRA GALFLGFLGAAGSTMGA VG |
| 14 | 1 | MRDNWRSELYKYKViVKIEPLGIAPTKAKRRVVQREKRA GAMFLGFLGAAGSTMGA VG |
| 3 | 1 | MRDNWRSELYKYKVvVKIEPLGIAPTKAKRRVVQREKRA ivGAmFLGFLGAAGSTMGA VG |
| 5 | 1 mgdpm MRDNWRSELYKYKVvVKIEPLGIAPTKAKRRVVQREKRAdlaVG i1GA1FLGFLGAAGSTMGA |
| | | +++ |

| | |
|---|---|
| 9 | 385 |
| 10 | 384 |
| 13 | 384 |
| 4 | 385 |
| 12 | 385 |
| 11 | 385 |
| 7 | 384 |
| 8 | 384 |
| 2 | 384 |
| 1 | 384 |
| 6 | 384 |
| 14 | 384 |
| 3 | 385 |
| 5 | 407 wqfgpg. |

|    | 1 | 2   | 3   | 4   | 5   | 6   | 7   | 8   | 9   | 10  | 11  | 12  | 13  | 14  |
|----|---|-----|-----|-----|-----|-----|-----|-----|-----|-----|-----|-----|-----|-----|
| 1  |   | 378 | 338 | 339 | 320 | 379 | 375 | 376 | 320 | 327 | 348 | 335 | 331 | 379 |
| 2  |   |     | 341 | 342 | 322 | 378 | 375 | 377 | 323 | 331 | 351 | 338 | 333 | 374 |
| 3  |   |     |     | 328 | 316 | 340 | 338 | 338 | 315 | 317 | 339 | 333 | 321 | 337 |
| 4  |   |     |     |     | 308 | 341 | 340 | 340 | 311 | 322 | 338 | 329 | 325 | 338 |
| 5  |   |     |     |     |     | 322 | 321 | 320 | 284 | 288 | 305 | 296 | 290 | 319 |
| 6  |   |     |     |     |     |     | 377 | 378 | 322 | 328 | 347 | 336 | 334 | 379 |
| 7  |   |     |     |     |     |     |     | 375 | 320 | 326 | 346 | 334 | 332 | 374 |
| 8  |   |     |     |     |     |     |     |     | 320 | 325 | 346 | 336 | 331 | 374 |
| 9  |   |     |     |     |     |     |     |     |     | 328 | 320 | 320 | 332 | 319 |
| 10 |   |     |     |     |     |     |     |     |     |     | 326 | 320 | 355 | 325 |
| 11 |   |     |     |     |     |     |     |     |     |     |     | 345 | 328 | 345 |
| 12 |   |     |     |     |     |     |     |     |     |     |     |     | 323 | 333 |
| 13 |   |     |     |     |     |     |     |     |     |     |     |     |     | 331 |
| 14 |   |     |     |     |     |     |     |     |     |     |     |     |     |     |

FIG. 4I

PSD301.PEP

```
         10         20         30         40         50         60         70
MGDPMMRDNW RSELYKYKVV KIEPLGIAPT KAKRRVVQRE KRADLAVGIL GALFLGFLGA AGSTMGARSL
linker├ HIV-1 env seq ——>                       +++
        80         90        100        110        120        130        140
TLTVQARQLL SGIVQQQNNL LRAIKDPKAQ QHLLQLTVWG IKQLQARVLA VERYLKDQQL LGIWGCSGKL
                         +++
       150        160        170        180        190        200        210
ICTTAVPWNA SWSNKSLEDI WNNMTWMQWE REINNYTNLI YSLLEESQNQ QEKNEQELLQ LDKWVDASLW
                                                                        ++
       220        230        240        250        260        270        280
NWSNITKWLW YIKLFIMIVG GLAGLRIVFA VLSIVNRVRQ GYSPLSFQTR LPNPRGPDRP EGIDEEGGER
                         *                                            *
       290        300        310        320        330        340        350
DRDRSTRLVD ISLALVWEDL RSLCLFSYHR LRDLLLIATR IVELLGRRGW EVLKYWWNLL QYVSQELKNS
           *                                                         *
       360        370        380        390        400        410
AVSLVNATAI AVAEGTDRVI EVVQRAYRAI RHIHRRIRQG LERILLQVHA SSLESSWQFG PG.
                                                  ├ linker seq ———
```

FIG. 7A

PSD302.PEP

```
            10         20         30         40         50         60         70
     MTMITPSLAA GPDTGHSSQV SQNYPIVQNI QGQMVHQAIS PRTLNAWVKV VEEKAFSPEV IPMFSALSEG
     linker seq————|—HIV-1 gag seq———→

```
         430        440        450        460        470        480        490
ERYLKDQQLL GIWGCSGKLI CTTAVPWNAS WSNKSLEDIW NNMTWMQWER EINNYTNLIY SLLEESQNQQ
         500        510        520        530        540        550        560
EKNEQELLQL DKWVDASLWN WSNITKWLWY IKLFIMIVGG LAGLRIVFAV LSIVNRVRQG YSPLSFQTRL
         ++                                  *
         570        580        590        600        610        620        630
PNPRGPDRPE GIDEEGGERD RDRSTRLVDI SLALVWEDLR SLCLFSYHRL RDLLLIATRI VELLGRRGWE
         *
         640        650        660        670        680        690        700
VLKYWWNLLQ YVSQELKNSA VSLVNATAIA VAEGTDRVIE VVQRAYRAIR HIHRRIRQGL ERILLQVHAS
         *            *                                                  └linker

RVIN.
```

FIG. 7C

```
829   CTaTACTCCATCCGCTGACCTGCTCCGTCCGTTCCTGACCCTGCAACTGATCTACCAGAACCTG   897
      LeuTyrSerIleAlaLeuThrCysSerValProPheLeuThrLeuGlnLeuIleTyrGlnAsnLeu

898   CGTGACTGGCTGCGTCTGCGCTTCCTGCAGTACGGCTGCGAATGGATTCAGGAAGCATTCCAa    966
      ArgAspTrpLeuArgLeuArgPheLeuGlnTyrGlyCysGluTrpIleGlnGluAlaPheGln

967   GCGGCCGCTCGTGCTACCCGTGAAACCCTGGCTGGCGCATGCCGTGGCCCTGTTCTGGAACGT   1035
      AlaAlaAlaArgAlaThrArgGluThrLeuAlaAlaCysArgGlyLeuTrpArgValLeuGluArg

Asp7181
                                                                     ↑
1036  ATCGGCCCGTGGTATCCTGGCTGTTCCGCGTATCCGTCGTCAGGGCGCCGAAATCGCTCTGCTGgtacca   1104
      IleGlyArgTrpTyrProArgArgIleArgArgGlnGlyAlaGluIleAlaLeuLeuValPro
                                                                    1099

HindIII
       |
1105  agctt   1109
      Ser
      1105
```

FIG. 9C

PSD306.PEP

```
        10         20         30         40         50         60         70
MSLKIYSSAH GRHTRGVFVL GFLGFLATAG SAMGAASLTV SAQSRTLLAG IVQQQQLLD VVKRQQELLR
linker |- HIV-2 TMP seq-->
        80         90        100        110        120        130        140
LTVWGTKNLQ ARVTAIEKYL QDQARLNSWG CAFRQVCHTT VPWVNDSLAP DWDNMTWQEW EKQVRYLEAN 150        160        170        180        190        200        210
ISKSLEQAQI QQEKNMYELQ KLNSWDIFGN WFDLTSWVKY IQYGVLIIVA VIALRIVIYV VQMLSRLRKG 220        230        240        250        260        270        280
YRPVFSSPPG YIQQIHIHKD RGQPANEETE EDGGSNGGDR YWPWPIAYIH FLIRQLIRLL TRLYSICRDL 290        300        310        320        330        340        350
LSRSFLTLQL IYQNLRDWLR LRTAFLQYGC EWIQEAFQAA ARATRETLAG ACRGLWRVLE RIGRGILAVP 360        370
RRIRQGAEIA LLVPSSWQFG PG.
            |linker--
```

FIG. 14A

PSD307.PEP

```
              10         20         30         40         50         60         70
     MTMITPSLAA GPDTGHSSQV SQNYPIVQNI QGQMVHQAIS PRTLNAWVKV VEEKAFSPEV IPMFSALSEG
     linker seq ├──HIV-1 gag seq──→
              80         90        100        110        120        130        140
     ATPQDLNTML NTVGGHQAAM QMLKETINEE AAEWDRVHPV HAGPIAPGQM REPRGSDIAG TTSTLQEQIG
             150        160        170        180        190        200        210
     WMTNNPPIPV GEIYKRWIIL GLNKIVRMYS PTSILDIRQG PKEPFRDYVD RFYKTLRAEQ ASQEVKNWMT
             220        230        240        250        260        270        280
     ETLLVQNANP DCKTILKALG PAATLEEMMT ACQGVGGPGH KARVLAEAMS QVTNTATIMM QRGNFRNQRK
             290        300        310        320        330        340        350
     MVKCFNCGKE GHTARNCRAL DLQPSLKIYS SAHGRHTRGV FVLGFLGFLA TAGSAMGAAS LTVSAQSRTL
                         linker        HIV-2 TMP seq ──→
             360        370        380        390        400        410        420
     LAGIVQQQQQ LLDVVKRQQE LLRLTVWGTK NLQARVTAIE KYLQDQARLN SWGCAFRQVC HTTVPWVNDS
```

FIG. 14B

```
          430        440        450        460        470        480        490
LAPDWDNMTW QEWEKQVRYL EANISKSLEQ AQIQQEKNMY ELQKLNSWDI FGNWFDLTSW VKYIQYGVLI
          500        510        520        530        540        550        560
IVAVIALRIV IYVVQMLSRL RKGYRPVFSS PPGYIQQIHI HKDRGQPANE ETEEDGGSNG GDRYWPWPIA
          570        580        590        600        610        620        630
YIHFLIRQLI RLLTRLYSIC RDLLSRSFLT LQLIYQNLRD WLRLRTAFLQ YGCEWIQEAF QAAARATRET
          640        650        660        670
LAGACRGLWR VLERIGRGIL AVPRRIRQGA EIALLVRVIN.
                                        └linker
PEP:
```

FIG. 14C

SYNTHETIC DNA DERIVED RECOMBINANT HIV ANTIGENS

This is division of U.S. patent application Ser. No. 08/314,570, filed Sep. 29, 1994, now U.S. Pat. No. 5,859,193 which is a continuation of U.S. patent application Ser. No. 08/066,610 filed May 24, 1993, now abandoned which is a continuation of U.S. patent application Ser. No. 07/895,187 filed Jun. 5, 1992, now abandoned which is a continuation of U.S. patent application Ser. No. 07/275,309, filed Nov. 23, 1988, now abandoned.

BACKGROUND OF THE INVENTION

The present invention relates to recombinant HIV (Human Immunodeficiency Virus) antigens. Recombinant antigens derived from the molecular cloning and expression in a heterologous expression system of the synthetic DNA sequences of the various HIV antigens can be used as reagents for the detection of antibodies and antigen in body fluids from individuals exposed to various HIV isolates.

The nucleotide sequence of the proviral genome has been determined for several HIV isolates, including HIV-1 strains HTLV-III (Ratner et al., *Nature* (1985) 313:277); ARV-2 (Sanchez-Pescador et al., *Science* (1985) 227:484); LAV (Wain-Hobson et al., *Cell* (1985) 40:9); and CDC-451 (Desai et al., *Proc. Natl. Acad. Sci. USA* (1986) 83:8380). The nucleotide sequence of the HIV-2 ROD isolate was reported by Guyader et al. (*Nature* (1987) 326:662).

HIV antigens have been obtained from the virus grown in tissue culture, or from a molecularly cloned genomic fragment expressed in heterologous hosts such as *Escherichia coli*. The tissue culture derived virus involves the cumbersome and often difficult process of growing virus infected cells in stringent sterile conditions. Further, the virus derived from tissue culture is infectious, and, therefore is hazardous to the health of individuals involved in propagation and purification. The expression of molecularly cloned HIV genomic fragments overcomes the biohazard problem. Generally, an HIV genomic fragment from a single HIV isolate with mammalian codons is expressed in a heterologous system, such as, bacteria or yeast, and is limited to the use of available restriction sites present in the viral genome for cloning and expression.

It has been difficut to obtain expression in heterologous systems of some of the HIV proteins, such as the HIV-1 envelope antigen gp41. Several researchers have tried deleting the hydrophobic regions of the HIV-1 gp41to increase expression levels. UK Patent Application GB 2188639 discloses an HTLV-III gag/env gene protein wherein the env fragment of the DNA sequence deleted codons corresponds to the first hydrophobic region of the gp41protein. U.S. Pat. No. 4,753,873 discloses a peptide fragment that are encoded by a nucleotide sequence wherein the nucleotides coding for a first and second hydrophobic region of HTLV-III gp41 are deleted.

Poor expression can be the result of many factors, including the specific nucleic acid sequence of the gene to be expressed, the fact that the mammalian codons of the gene sequence to be expressed may not be efficiently transcribed and translated in a particular heterologous system, and the secondary structure of the transcribed messenger RNA. The use of synthetic DNA fragments can increase expression in heterologous systems.

SUMMARY OF THE INVENTION

Recombinant antigens which are derived from the molecular cloning and expression of synthetic DNA sequences in heterologous hosts are provided. Synthetic DNA sequences coding for the recombinant antigens of the invention are further provided. The synthetic DNA sequences selected for expression of various HIV antigens are based on the amino acid sequence of either a single isolate or several isolates, optimized for expression in *Escherichia coli* by specific codon selection. The synthetic DNA sequence gives higher expression of the particular antigen encoded. These antigens can be substituted for viral antigens derived from tissue culture for use as diagnostic and therapeutic reagents.

The present invention can be utilized to synthesize full length HIV transmembrane envelope gene using bacterial codons. Another aspect of the invention involves the linkage of sequences which are poorly expressed as individual proteins, to sequences which are expressed with high efficiency. The combination of the sequence of the entire coding region of a gene of one virus with coding sequences of another gene from a different virus to produce a fusion protein can be achieved. The fusion proteins thus expressed have a unique advantage of antigenic epitopes of two viral antigens.

The present invention includes full length synthetic genes (FSG) for HIV-1 and HIV-2 transmembrane glycoprotein (TMP).

DESCRIPTION OF THE DRAWINGS

FIG. 1 illustrates the alignment of the TMP fragment encoding amino acid residue nos. 552–668 of HIV-1 with the sequences of the four different isolates used to derive the amino acid sequence of BS2-10.

FIG. 4 is a comparison of the amino acid sequence used to develop the synthetic HIV-1 envelope gene with known amino acid sequences of 13 independent isolates, indicating all linker-derived sequences (+) and amino acid substitutions (*).

FIG. 7 illustrates the amino acid sequences of pSD301 and pSD302, indicating all linker-derived sequences (+) and amino acid substitutions (*).

FIG. 14 indicates the specific amino acid sequences of pL constructs pSD306 and pSD307 indicating all linker sequences, HIV-1 gag sequences, and HIV-2 TMP sequences.

FIGS. 15A and 15B illustrate results of expression analysis of pSD306 in *E. coli* CAG456 cells, wherein FIG.15A shows a Coomassie stained gel and FIG.15B shows an Immunoblot using HIV-2 positive human sera.

FIGS. 16A and 16B illustrate results of expression analysis of pSD307 in *E. coli* pRK248.clts/RR1 cells, wherein FIG. 16A shows a Coomassie stained gel and FIG. 16B shows an Immunoblot using HIV-2 positive human sera.

DETAILED DESCRIPTION OF THE INVENTION

Synthetic DNA fragments of the HIV genome can be synthesized based on their corresponding amino acid sequences. By comparing the particular region of interest between different isolates, a sequence can be selected which is different from any sequence that exists in nature, because the sequence is a compilation of the sequences from various isolates. For example, the synthetic HIV-1 envelope protein described in Example 1, is based on the amino acid sequence of four different HIV 1 isolates, namely, HTLV-IIIB, LAV-1, ARV-2 and CDC-451.

Other properties can be built into the sequence. For example, codons can be switched for optimal expression in bacteria or yeast, specific restriction sites can be introduced, and other restriction sites can be removed. In addition, the sequence should have specific restriction sites at both 5' and 3' ends of the fragment to facilitate cloning in a particular vector. Synthetic DNA fragments can be synthesized as follows: (1) select an unique protein sequence, (2) reverse translate to determine complementary DNA sequence, (3) optimize codons for bacterial or yeast expression, and (4) introduce and/or remove specific restriction sites.

Sixty-one distinct nucleotide codons code for 20 amino acids giving rise to the degeneracy in the genetic code. Researchers have reported the frequencies of codons used in nucleic acids for both eukaryotic and prokaryotic organisms. (Grantham et al., *Nucleic Acids Res.* [1980] 9:r43; Gouy et al., *Nucleic Acids Res.* [1982] 10:7055; Sharp et al., *Nucleic Acids Res.* [1986] 14:7737.) Sequences from the entire *E. coli* genome, with examples of sequences from the chromosome, transposons, and plasmids, have been analyzed. These sequences code for structural proteins, enzymes and regulatory proteins. Correlation has been shown between the degree of codon bias within a particular gene and the level of gene expression.

It is preferred that the same codon triplet for each particular amino acid of the synthetic DNA sequence be used. However, alternative codon(s) can be used to add or delete a particular restriction site. The sequence should include unique restriction sites which can be used to delete a specific fragment or sequence, or substitute a particular sequence in case of an error in the original synthesis.

Vector systems which can be used include plant, bacterial, yeast, insect, and mammalian expression systems. It is preferred that the codons are optimized for expression in the system used. The proteins and polypeptides provided by the invention, which are cloned and expressed in heterologous systems, as described above, can be used for diagnostic and therapeutic purposes.

A preferred expression system utilizes the lambda pL vector system. This expression system has the following features: (1) a strong lambda pL promoter, (2) a strong three-frame translation terminator rrnBt1, and (3) translation starts at an ATG codon, eight base pairs from the ribosome binding site located within an accessible NcoI restriction site.

Another advantage of the expression system of the present invention is that one can customize the synthetic DNA fragments so they contain specific DNA sequences which express proteins with desired amino acid sequences, and further allows one the capability of adding, at either the 5' or 3' end, other DNA sequences to facilitate the transfer of synthetic fragments into various vectors.

Additionally, the use of particular restriction sites at both ends of the fragment may also facilitate incorporation of the fragment into other sequences to generate fusion proteins, which can also be used as diagnostic and therapeutic reagents. For example, the HIV-1 gp41 sequence can be incorporated within or at the end of core/surface antigen of the hepatitis B viral sequence to generate a fusion protein which can be used in a single assay screening system for the detection of both AIDS and Hepatitis B in prospective blood donors. Alternatively, the assay can be used to track the course of a patient's infection.

Other proteins from any source, including bacterial, yeast, insect, plant or mammalian, can be used with the synthetic DNA fragments of the invention to produce fusion proteins. Those which are expressed efficiently in their respective expression systems are especially preferred because they can enhance the expression of the synthetic fragment of the fusion protein.

The synthetic DNA sequences of the present invention, derived from several HIV isolates and optimized for expression in *E. coli.* provides continuous availability and uniformity of HIV antigen preparations which will recognize test sera from individuals exposed to genetically distinguishable variant HIV isolates. The recombinant antigen expression Is very stable since *E. coli* codons have been used for its synthesis. Moreover, the insertion of specific restriction sites allows addition, deletion, or substitution in important antigenic epitopes in the coding sequences, a property difficult to achieve when naturally occurring HIV sequences are utilized for expression. Construction of synthetic genes also allows the addition of protein sequences at either amino- or carboxyl-terminus of the gene thereby allowing the development of novel reagents. For example, a fusion gene can be produced comprising a fusion between HIV-1 core antigen and HIV-1 envelope synthetic gene. More specifically the envelope synthetic gene comprises the carboxyl-terminus HIV-1 gp120 sequence and the full length HIV-1 gp41. Similarly, the HIV-1 core antigen DNA sequence can be fused to the HIV-2 gp41 sequences, both of which can be expressed at high levels in heterologous host systems such as *E. coli.*

*E. coli* strains containing plasmids useful for constructs of the invention have been deposited at the American Type Culture Collection, 12301 Parklawn Drive, Rockville, Md., on Nov. 22, 1988, under the accession nos. ATCC 67855 (pSD301/RR1/pRK248.clts) and ATCC 67856 (pSD306/CAG456).

The following examples further describe the invention. The examples are not intended to limit the invention in any manner.

Reagents and Enzymes

Figure 2:
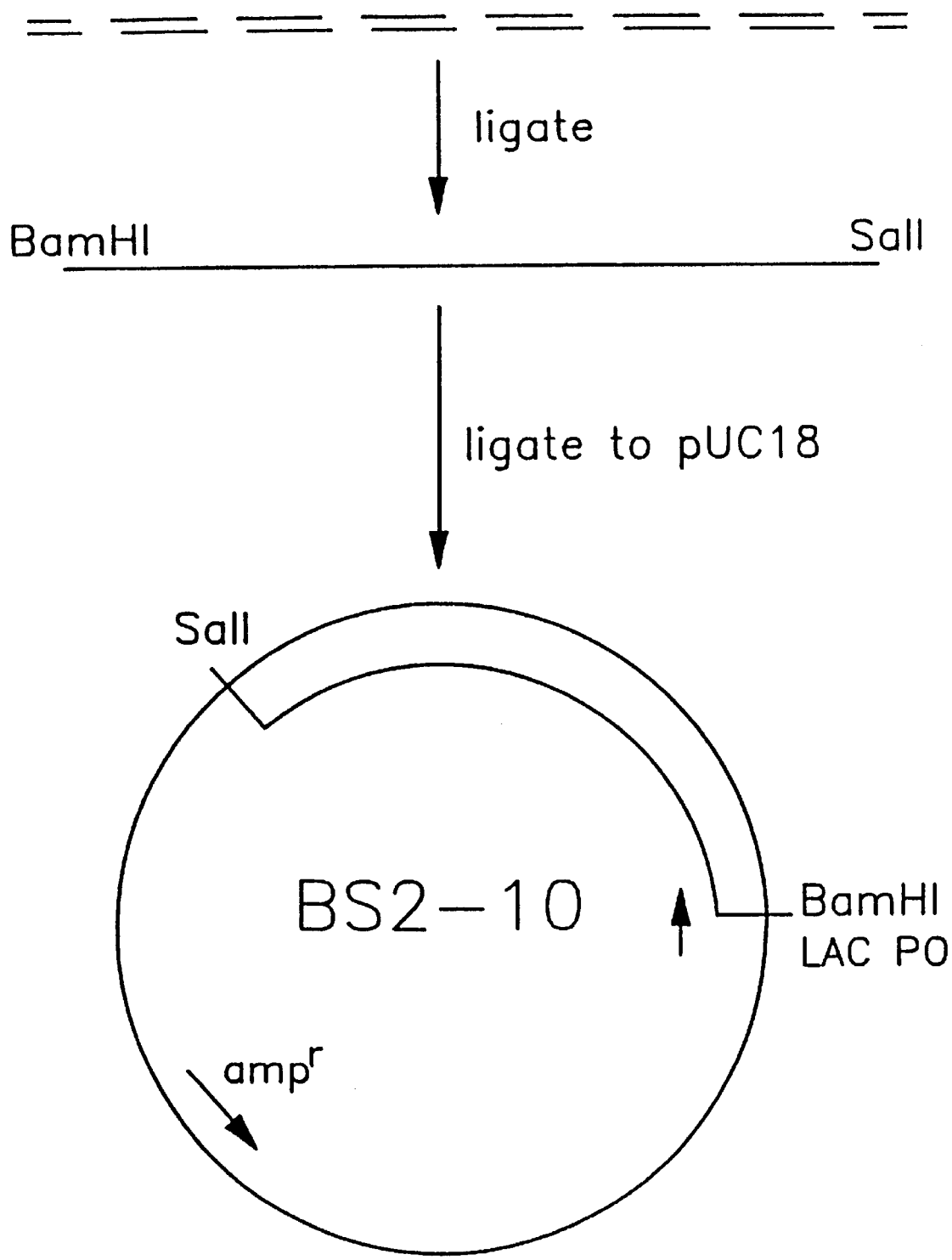
FIG. 2 illustrates the assembly of 16 oligonucleotides to form the synthetic TMP fragment of FIG. 1, and its cloning into pUC18, designated BS2-10.
Figure 3B:
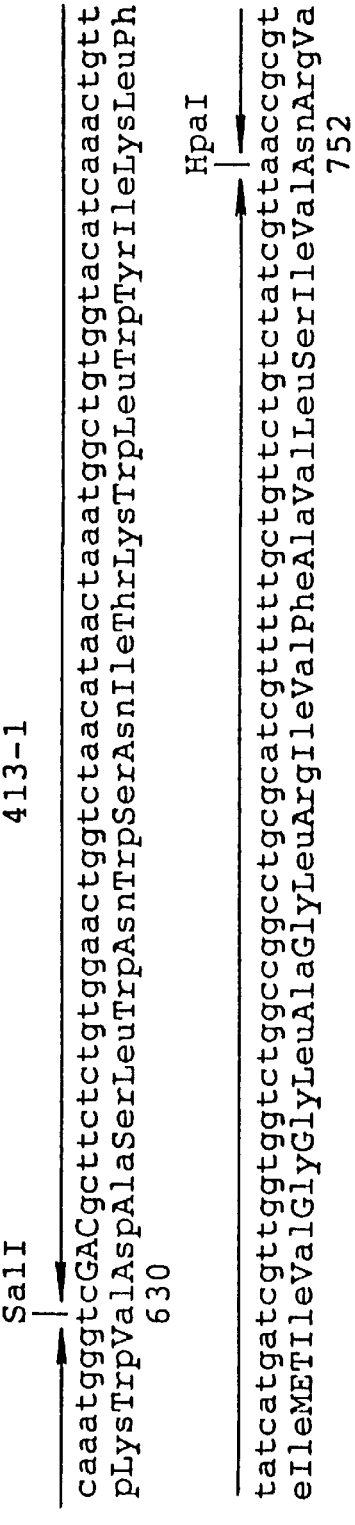
FIG. 3 illustrates the DNA and amino acid sequence of FSG, indicating the restriction sites and subfragments used for assembly.
Figure 5:
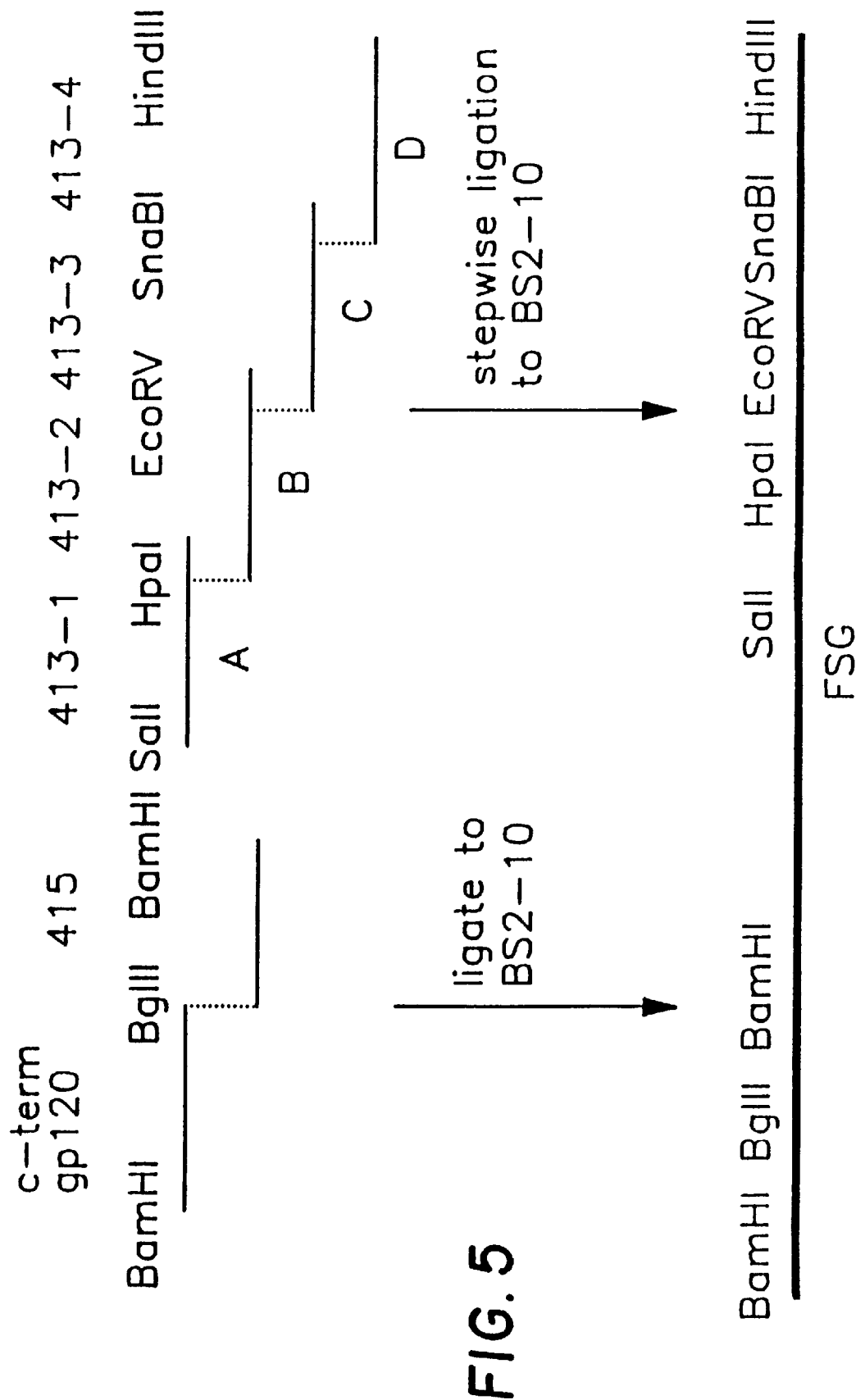
FIG. 5 is a schematic diagram of the assembly and cloning of the major subfragments to form FSG in pUC18.
Figure 6:
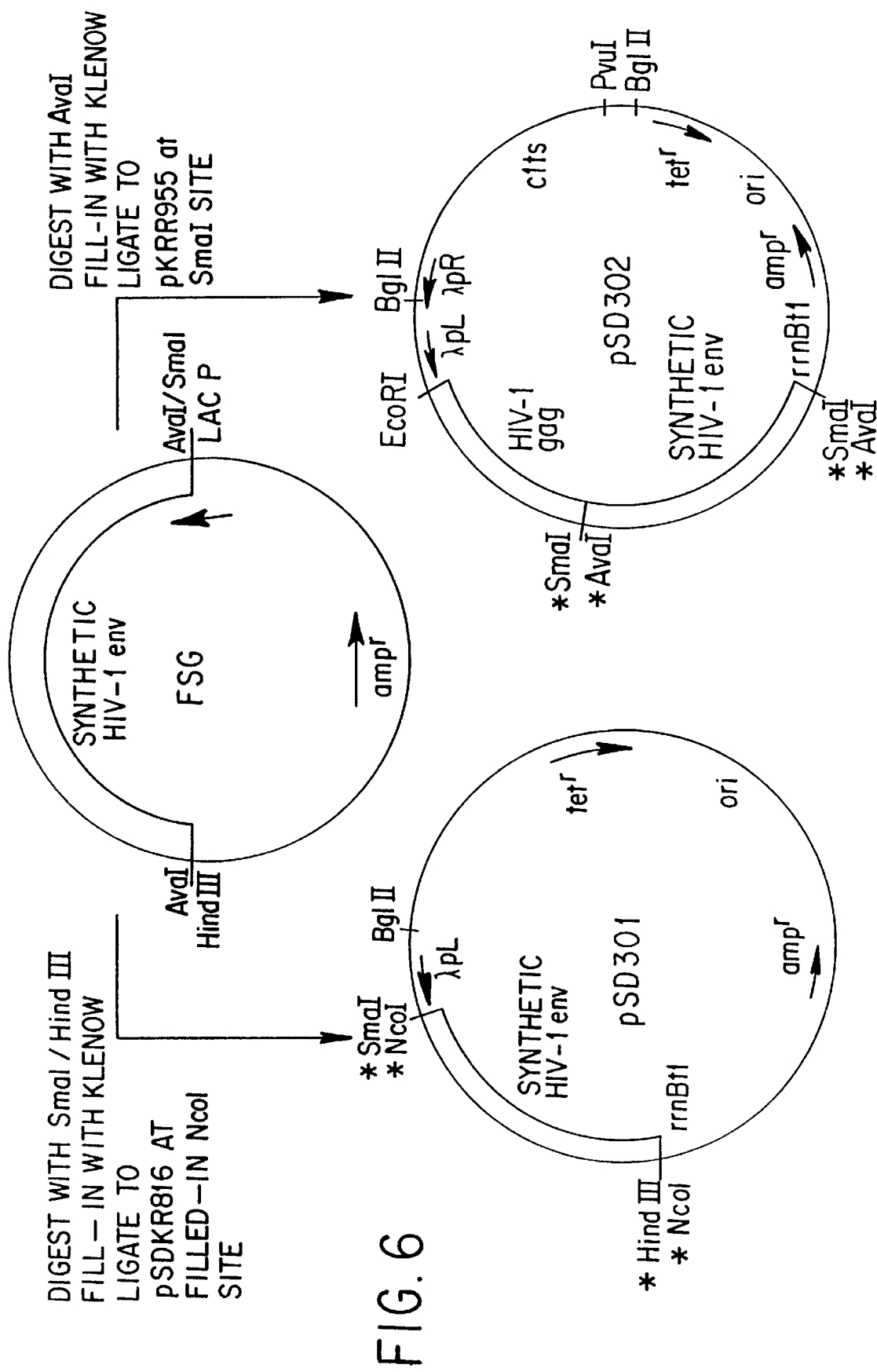
FIG. 6 is a schematic diagram of the cloning of FSG into lambda pL expression vectors to generate pSD301 and pSD302.

Media such as Luria-Bertani (LB) and Superbroth II (Dri Form) were obtained from Gibco Laboratories Life Technologies, Inc., Madison, Wis. Restriction enzymes, Klenow fragment of DNA polymerase I, T4 DNA ligase, T4 polynucleotide kinase, nucleic acid molecular weight standards, M13 sequencing system, X-gal (5-bromo-4-chloro-3-indonyl-β-D-galactoside), IPTG (isopropyl-β-D-thiogalactoside), glycerol, Dithiothreitol, 4-chloro-1-napthol were purchased from Boehringer Mannheim Biochemicals, Indianapolis, Ind.; or New England Biolabs, Inc., Beverly, Mass.; or Bethesda Research Laboratories Life Technologies, Inc., Gaithersburg, Md. Prestained protein molecular weight standards, acrylamide (crystallized, electrophoretic grade >99%); N-N'-Methylene-bis-acrylamide (BIS); N,N,N',N',-Tetramethylethylenediamine (TEMED) and sodium dodecylsulfate (SDS) were purchased from BioRad Laboratories, Richmond, Calif. Lysozyme and ampicillin were obtained from Sigma Chemical Co., St. Louis, Mo. Horseradish peroxidase (HRPO) labeled secondary antibodies were obtained from Kirkegaard & Perry Laboratories, Inc., Gaithersburg, Md. Seaplaque® (low melting point agarose, available from FMC Bioproducts, Rockland, Me.) agarose (low melting agarose) was purchased from FMC Bioproducts, Rockland, Me.

T50E10 contained 50 mM Tris, pH 8.0, 10 mM EDTA; 1×TG contained 100 mM Tris, pH 7.5 and 10% glycerol; 2×SDS/PAGE loading buffer consisted of 15% glycerol, 5% SDS, 100 mM Tris base, 1M β-mercaptoethanol and 0.8% Bromophenol blue dye; TBS contained 50 mM Tris, pH 8.0, and 150 mM sodium chloride; Blocking solution consisted of 5% Carnation nonfat dry milk in TBS.

Host Cell Cultures. DNA Sources and Vectors

*E. coli* JM103 cells, pUC8, pUC18, pUC19 and M13 cloning vectors were purchased from Pharmacia LKB Biotechnology, Inc., Piscataway, N.J.; Competent Epicurean™ coli strains XL1-Blue and JM109 were purchased from Stratagene Cloning Systems, La Jolla, Calif. RR1 cells were obtained from Coli Genetic Stock Center, Yale University, New Haven, Conn.; and *E. coli* CAG456 cells from Dr. Carol Gross, University of Wisconsin, Madison, Wis. Vector pRK248.clts was obtained from Dr. Donald R. Helinski, University of California, San Diego, Calif.

General Methods

All restriction enzyme digestions were performed according to suppliers' instructions. At least 5 units of enzyme were used per microgram of DNA, and sufficient incubation was allowed to complete digestions of DNA. Standard procedures were used for mini cell lysate DNA preparation, phenol-chloroform extraction, ethanol precipitation of DNA, restriction analysis of DNA on agarose, and low melting agarose gel purification of DNA fragments (Maniatis et al., *Molecular Cloning. A Laboratory Manual* [New York: Cold Spring Harbor, 1982]). Plasmid isolations from *E. coli* strains used the alkali lysis procedure and cesium chloride-ethidium bromide density gradient method (Maniatis et al., supra). Standard buffers were used for T4 DNA ligase and T4 polynucleotide kinase (Maniatis et al., supra).

EXAMPLES

Example 1

Cloning Strategy of Codon-optimized Synthetic HIV-1 Envelope Protein

In order to develop a synthetic gene encoding the HIV-1 envelope glycoprotein and fragments thereof, the amino acid sequences of four independent HIV-1 viral isolates designated as HTLV-IIIB (BH102), LAV-1 (MAL), ARV-2 (SF), and CDC-451 (CDC42) were compared. A unique amino acid sequence from the four isolates (FIG. 1) was selected to derive a fragment with amino acid residues nos. 552–668 (numbering by Ratner et al., supra). This fragment contained nine amino acid substitutions (8%) as compared to the HTLV-IIIB (BH102) isolate. This amino acid sequence was reverse translated using codons optimized to facilitate high level expression in *E. coli.* The ambiguous nucleotides remaining in the second and/or third base of the codon were assigned to facilitate molecular cloning, and the addition, substitution, or deletion of sequences. The DNA sequence was then subdivided into eight double stranded fragments with unique 6 bp overhangs to direct specific annealing. The sixteen individual oligonucleotides were synthesized on Applied Biosystem 380A DNA synthesizer using methods and reagents recommended by the manufacturer. These purified oligonucleotides were annealed and ligated together to assemble the entire fragment which was digested with BamHI and SalI, ligated into pUC18 and transformed into *E. coli* JM103 cells. A clone designated BS2-10 (FIG. 2) was isolated, restriction mapped and its DNA sequence confirmed using the Sanger dideoxy chain termination method (Sanger et al., *J. Mol. Biol.* (1982) 162:729).

In order to establish that clone BS2-10 expressed this unique HIV-1 transmembrane protein (TMP) fragment, the BS2-10/JM103 culture was grown at 37° C. in 50 ml Luria Broth, in a 250 ml Erlenmeyer flask. When the cultures reached an OD600 of 0.3–0.5, IPTG was added to a final concentration of 1 mM to induce expression. Samples (1.5 ml) were removed at 1 hr intervals, and the cells were pelleted and resuspended to an OD600 of 10.0 in 2×SDS/PAGE loading buffer. Aliquots (15 μl) of the prepared samples were loaded on a 15% SDS/PAGE gel, and the proteins were separated and then electrophoretically transferred to nitrocellulose for immunoblotting. The nitrocellulose sheet containing the transferred proteins was incubated with Blocking Solution for one hour and incubated overnight at 4° C. with AIDS patients' sera diluted in TBS containing 5% *E. coli* JM103 lysate. The nitrocellulose sheet was washed three times in TBS, then incubated with HRPO-labeled goat anti-human IgG, diluted in TBS containing 10% fetal calf sera. The nitrocellulose was washed three times with TBS and the color was developed in TBS containing 2 mg/ml 4-chloro-1-napthol, 0.02% hydrogen peroxide and 17% methanol. Clone BS2-10 demonstrated a strongly immunoreactive band with AIDS patients' sera indicating that the synthetic HIV-1 TMP fragment was expressed in *E. coli.* In order to assemble the full length HIV-1 transmembrane protein, as well as the extreme carboxyl-terminal 37 amino acids of gp120, the amino acid sequences of the four isolates described previously were compared to each other to derive a unique amino acid sequence for this gene. After this unique amino acid sequence was reverse translated using codons optimized for *E. coli* expression, the ambiguous nucleotides were assigned as previously described. The full length synthetic HIV-1 envelope gene (FSG) was divided into six additional subfragments. The complete DNA and amino acid sequence of FSG is shown in FIG. 3, indicating the restriction sites and subfragments used for assembly. FIG. 4 is a comparison of the amino acid sequence used to develop the synthetic HIV-1 envelope gene with known amino acid sequences of 13 independent isolates reported in the Los Alamos HIV Data Bank (Meyers et al., *Human Retroviruses and AIDS* (1987), Los Alamos National Laboratory). The Genalign program of Intelligenetics was used to align these sequences, and the alignment demonstrates that FSG (designated SYNGENE in FIG. 4) retains substantial overall sequence homology compared to other known isolates. Alignment parameters and alignment scores of the individual sequences are also shown.

Synthesis and Cloning of Subfragments

The subfragments located downstream from BS2-10, designated 413-1 through 413-4, were synthesized along with additional sequences containing a BamHI restriction site at the 5' end and a HindIII restriction site at the 3' end to facilitate molecular cloning and DNA sequence analysis of the individual subfragments. The subfragments located upstream of BS2-10 were also synthesized with additional sequences containing restriction sites useful for cloning and DNA sequence analysis. The subfragment encoding the carboxyl-terminal gp120 amino acid sequence, designated c-term gp120, contained EcoRI and BamHI restriction sites on the 5' end and BglII and SmaI restriction sites on the 3' end. Similarly, subfragment 415 contained a BglII site on the 5' end and BglII and BamHI restriction sites on the 3' end. With the exception of the c-term gp120 subfragment, in which both strands were synthesized as described for BS2-10, the remaining subfragments of FSG were synthesized by a method utilizing the Klenow fragment of DNA polymerase I. In this method, oligonucleotides comprising opposite strands of a particular subfragment, which contained ten complementary bases, were synthesized and annealed. The second complementary strand was then filled in by the Klenow fragment of DNA polymerase I in the presence of the four deoxynucleotides in a manner similar to that described by Sanger et al., supra, for DNA sequencing. The resulting double-stranded subfragment was then digested with the appropriate restriction enzymes and cloned into pUC vectors to confirm the DNA sequence, as previously described. Subfragments 413-1 through 413-4 were cloned into pUC18 using the BamHI and HindIII restriction sites common to all. Subfragment c-term gp120 was cloned into pUC8 using the EcoRI and SmaI restriction sites. Subfragment 415 was cloned into the plasmid containing c-term gp120 at the BglII restriction site and screened for proper orientation by restriction mapping. The plasmid DNAs for all subfragments were prepared by the cesium chloride buoyant density gradient method and the individual DNA sequences were confirmed directly from the double-stranded template (Hattori et al., *Nucl. Acid Res.* (1985) 13:7813).

Assembly and Cloning of FSG

Subfragments located downstream from BS2-10 were cloned in a stepwise fashion utilizing unique Internal restriction sites at the 5' end and a common HindIII site at the 3' end. For example, subfragment 413-1 was cloned into BS2-10 at the SalI and HindIII restriction sites to generate clone BS2-10A, into which 413-2 was inserted at the HpaI and HindIII restriction sites to generate clone BS2-10B. Similarly, subfragments 413-3 and 413-4 were added using unique EcoRV and SnaBI restriction sites, respectively. The two subfragments located upstream of clone BS2-10, having been cloned together in pUC8, were ligated to BS2-10 as a BamHI fragment. FIG. 5 shows the cloning method used to assemble the synthetic HIV-1 envelope gene in pUC18. The final clone, designated FSG, was restriction mapped to confirm the proper orientation of the BamHI-BamHI fragment.

Example 2

Cloning and Expression of FSG in Lambda pL Vector Systems

Expression analysis of FSG was carried out in vector systems utilizing the strong lambda pL promoter and the temperature sensitive cI repressor gene (Benard et al., *Gene* (1979) 5:59). The specific vectors used in these analyses are derivatives of pBR322, containing a lambda pL promoter and a synthetic Shine-Dalgarno sequence, followed by restriction sites used for cloning various genes of interest. In addition, these vectors contain the strong three-frame translation terminator rrnBt1. Vector pSDKR816 contains a NcoI restriction site which provides an ATG start codon optimally spaced from the start of transcription. FIG. 6 schematically presents the cloning of FSG into pSDKR816 to generate clone pSD301. Briefly, FSG was digested with HindIII and SmaI, the ends were made blunt by filling in with the Klenow fragment of DNA polymerase I, and the 1209 bp fragment was purified and ligated into pSDKR816 at the NcoI site filled in with the Klenow fragment of DNA polymerase I. After transformation into *E. coli* RR1 cells containing the clts gene on the compatible vector pRK248, a clone with FSG in the proper orientation was isolated by restriction mapping and designated pSD301. The specific amino acid sequence encoded by pSD301 is presented in FIG. 7 indicating all linker derived sequences (+) and all amino acid substitutions within the HIV-1 envelope sequences not yet identified in any published sequence (*).

Additionally, FSG was cloned as a fusion to the HIV-1 gag protein (amino acid residue nos. 121–407, numbering by Ratner et al., supra) which is highly expressed under control of the lambda pL promoter in vector pKRR955. FSG was digested with AvaI, the ends were made blunt by filling in with the Klenow fragment of DNA polymerase I, and the 1199 bp fragment was purified and ligated into pKRR955 at the SmaI restriction site to form an HIV-1 gag/synthetic env fusion protein (FIG. 6). After transformation into *E. coli* pRK248.clts/RR1 cells, a clone containing FSG in the proper orientation was identified by restriction mapping and designated pSD302. The specific amino acid sequence of this fusion protein is presented in FIG. 7 indicating all linker derived sequences, HIV-1 gag sequences, and HIV-1 envelope sequences as previously described.

Fifty ml cultures of pSD301 and pSD302 in *E. coli* pRK248.clts/RR1 cells were grown in Superbroth II media at 30° C. to an OD600 of 0.5, at which time the cultures were shifted to 42° C. to inactivate the temperature sensitive cI repressor and thereby induce expression of the lambda pL promoter. Two samples (2.0 ml each) were removed at 1 hr intervals. Sample preparation was as follows.

The cells were pelleted, then resuspended in either 1×TG buffer or T50E10 buffer. An equal volume of 2×SDS/PAGE loading buffer was added to the 1×TG suspended cells to produce the whole lysate. The sample resuspended in T50E10 was sonicated eight times for 30 seconds each, at a power setting of 10 watts, using the microtip provided with the Vibra Cell Sonicator (Sonics and Materials, Inc., Danbury, Conn.). The sonicated sample was then centrifuged to remove the insoluble fraction which was resuspended in the original starting volume of T50E10. An equal volume of 2×SDS/PAGE loading buffer was added to both the sonicated soluble and insoluble fractions, which together with the whole cell lysate, were boiled for 5 min, centrifuged to remove any remaining insoluble material, and aliquots (15 μl) were separated on duplicate 12.5% SDS/PAGE gels. Proteins from one such gel were electrophoretically transferred to nitrocellulose for immunoblotting with AIDS patients' sera, as previously described. The second gel was fixed in a solution of 50% methanol, 10% acetic acid for twenty minutes at room temperature, and then stained with 0.25% Coomassie blue dye in a solution of 50% methanol, 10% acetic acid for 30 minutes. Destaining was carried out using a solution of 10% methanol, 7% acetic acid for 3–4 hr, or until a clear background was obtained.

Figure 8A:
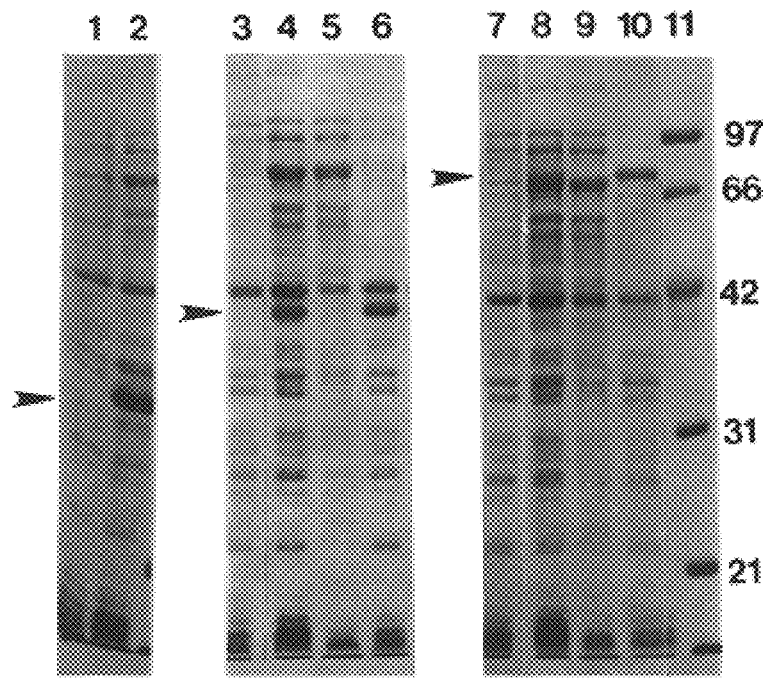
FIG. 8 illustrates results of expression analysis of pSD301 and pSD302. A) Coomassie stained gel; B) Immunoblot using AIDS patients' sera.
Figure 8B:
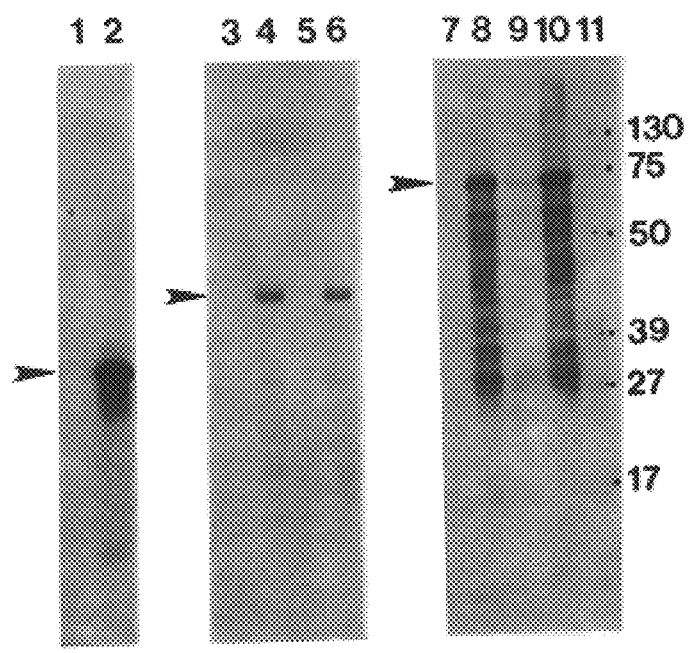

FIG. 8 presents the expression of pSD301 and pSD302 prior to (T0) and four hours post (T4) induction, analyzed by Coomassie blue staining (FIG. 8A) and immunoblotting (FIG. 8B). Samples were pKRR955 (T0 whole cell lysate [lane 1], T4 whole cell lysate [lane 2]); pSD301 (T0 whole cell lysate [lane 3], T4 whole cell lysate [lane 4], T4 sonicated soluble fraction [lane 5], and T4 sonicated insoluble fraction [lane 6]); and pSD302 (T0 whole cell lysate [lane 7], T4 whole cell lysate [lane 8], T4 sonicated soluble fraction [lane 9], and T4 sonicated insoluble fraction [lane 10]). Molecular weight standards were run in lane 11. Arrows indicate the position of the induced proteins which are clearly visualized in both the whole cell lysate and the sonicated insoluble cell fraction by Coomassie blue staining (FIG. 8A). Lane 2 indicates that pKRR955 expressed the HIV-1 gag protein at a level greater than 25% of total cellular protein, lane 4 indicates that pSD301 expressed the synthetic HIV-1 envelope protein at a level of approximately 12% of total cellular protein, and lane 8 indicates that pSD302 expressed the HIV-1 gag/synthetic env fusion protein at a level of approximately 5% of total cellular protein. The expression levels obtained using FSG were significantly higher than those obtained using the corresponding native viral DNA sequences in similar pL vector systems. All three recombinant proteins were highly reactive with AIDS patients' sera (FIG. 8B). This data demonstrates that the synthetic HIV-1 envelope gene, including the hydrophobic region of the transmembrane protein, can be efficiently expressed in *E. coli* and the expressed proteins are highly immunoreactive.

Example 3

Synthesis and Cloning of Synthetic HIV-2 TMP and Fragment Thereof

Figure 9A:
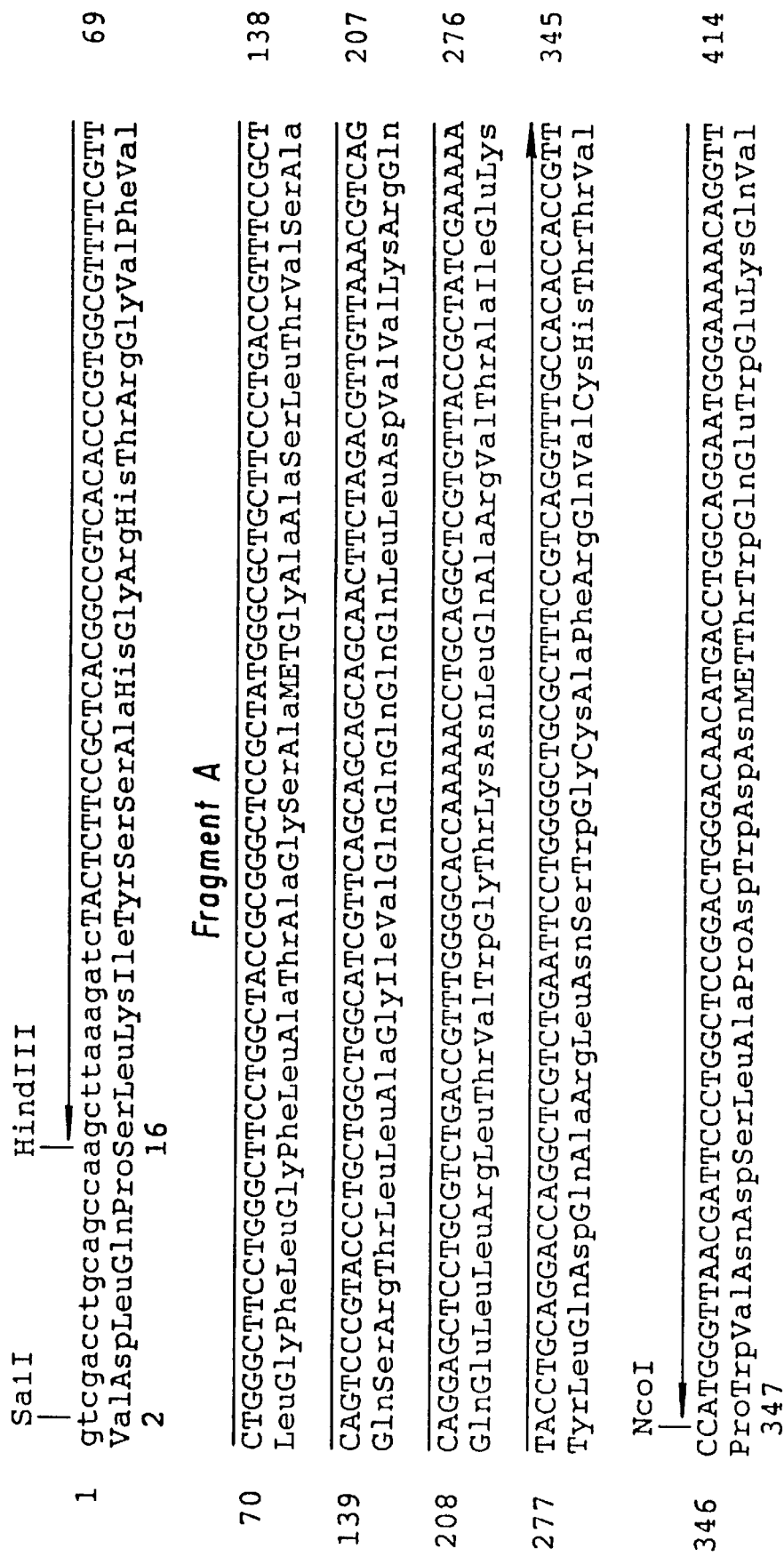
FIG. 9 illustrates the DNA and amino acid sequence of the full length synthetic HIV-2 TMP, indicating restriction enzymes used to assemble the gene including linker sequences at both ends to facilitate cloning.
Figure 9B:
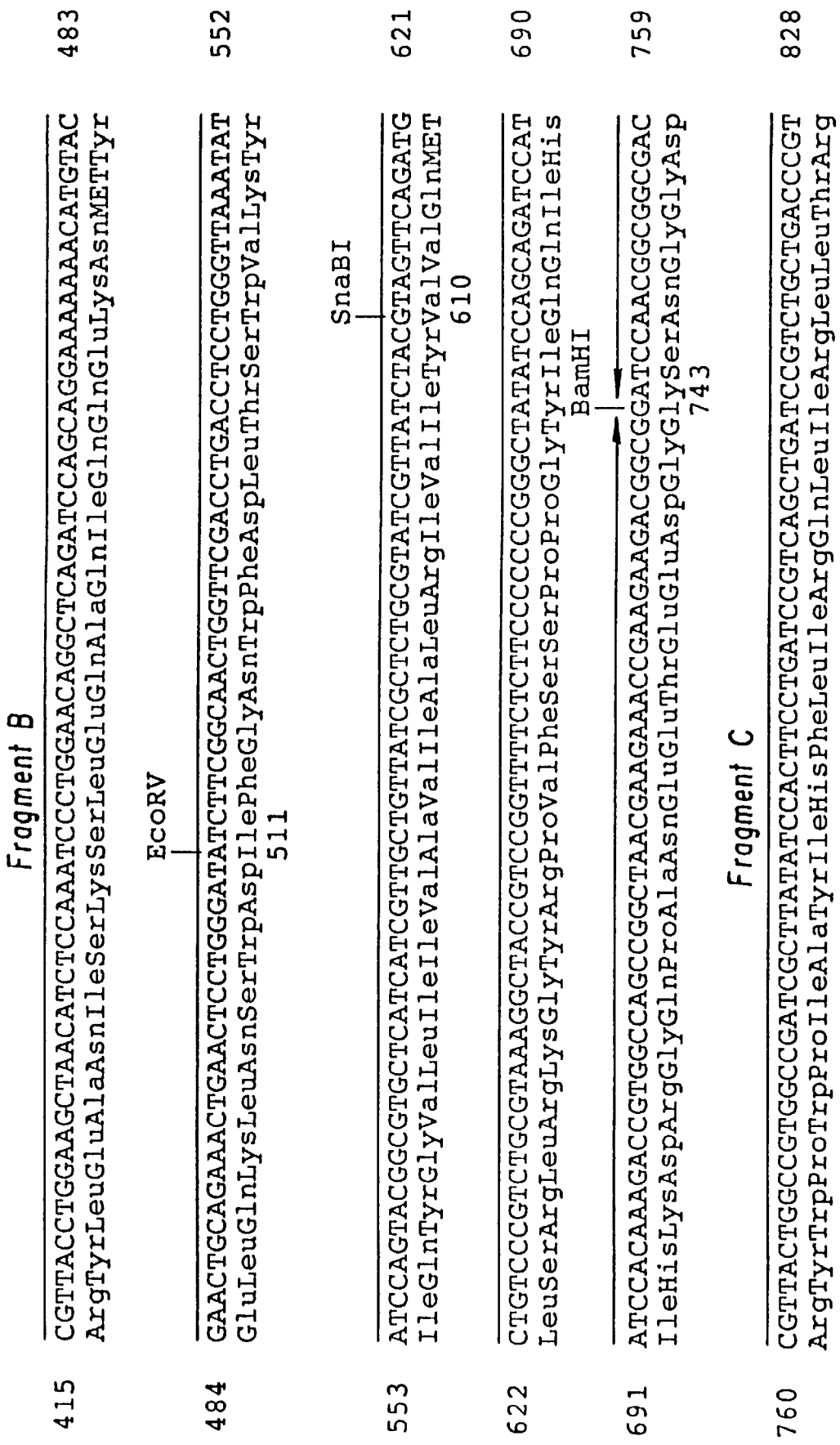
Figure 10:
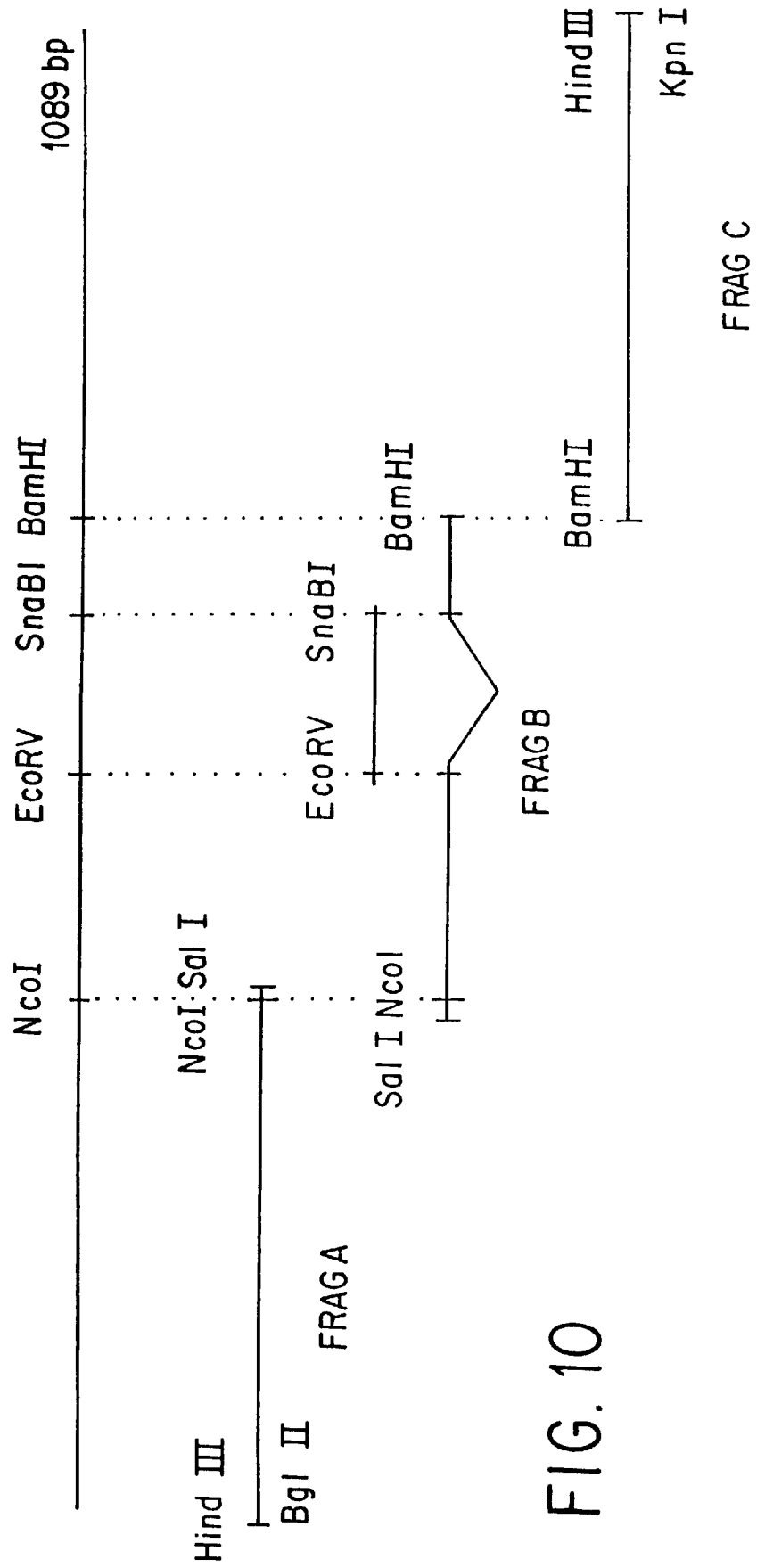
FIG. 10 illustrates the three major subfragments used to construct the synthetic HIV-2 TMP gene.
Figure 11:
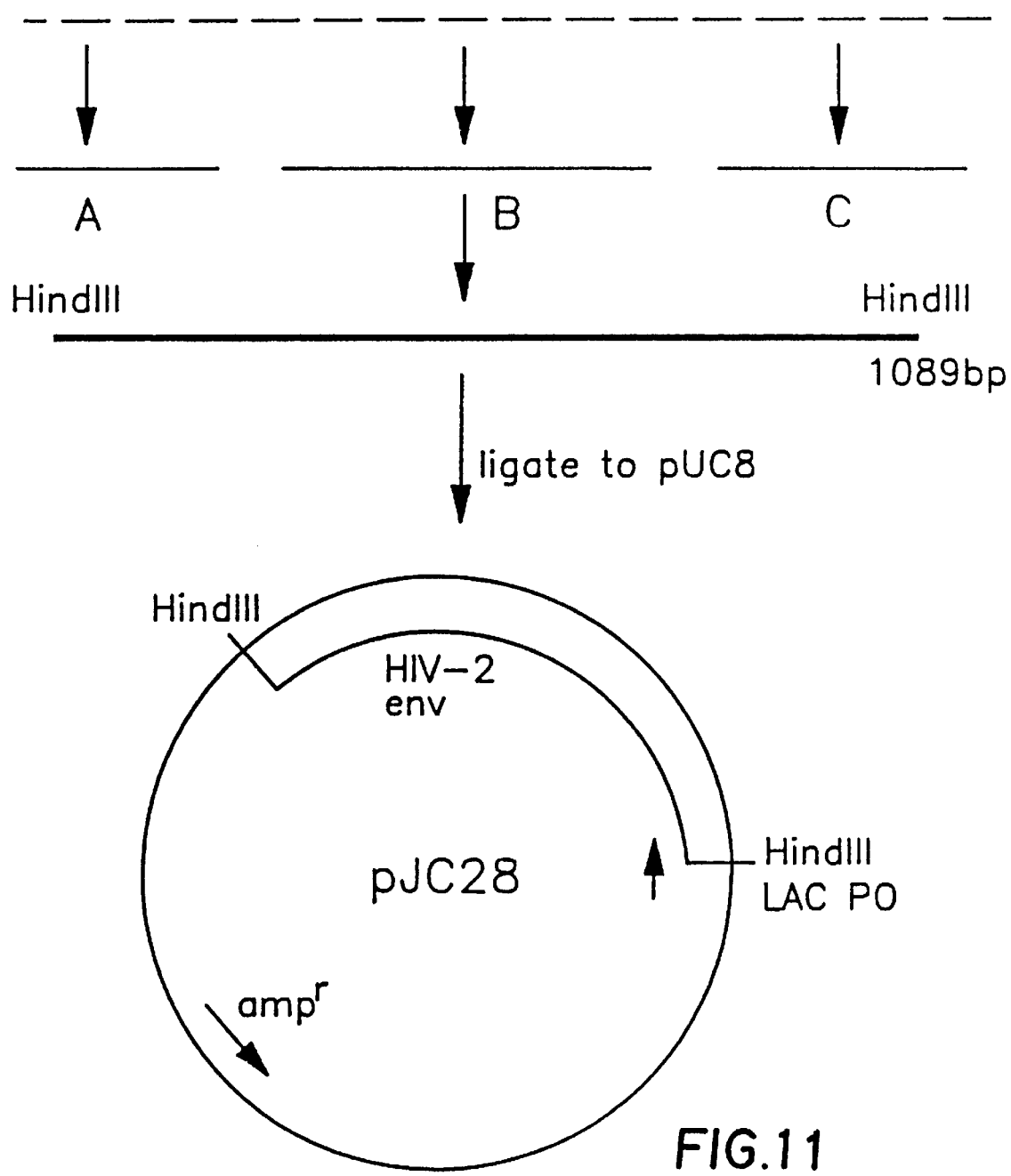
FIG. 11 is a schematic diagram of the assembly of the major subfragments to form the full length synthetic HIV-2 TMP and its cloning into pUC8 to generate pJC28.

The entire HIV-2 transmembrane protein (TMP) was chemically synthesized using the method of oligonucleotide directed double-stranded break repair disclosed in U.S. Pat. application Ser. No. 883,242, filed Jul. 8, 1986 by Mandecki (EPO 87109357.1), as follows. Within an appropriate host cell, target DNA having a double-strand break was cocultivated with an oligonucleotide having a nucleotide sequence complementary to a strand of the target DNA on both sides of the break wherein the oligonucleotide includes a first portion completely complementary to the nucleotide sequence of a first region of the strand and located on a first side of the double-strand break, and a second portion completely complementary to the nucleotide sequence of a second region of the strand and located on a second side of the double-strand break. The host cell was maintained under appropriate conditions and for a period sufficient to permit repair of the double-strand break. Envelope amino acid residues 502–858 of the HIV-2 ROD isolate (numbering by Guyader et al., supra) were reverse translated using codon assignments optimal for expression in *E. coli*. After specific nucleotides were assigned to the remaining ambiguous nucleotides, as previously described, the full length TMP sequence was generated as indicated in FIG. 9. The synthetic gene was assembled and cloned as three separate subfragments represented by fragment A, a 335 bp HindIII-NcoI fragment, fragment B, a 309 bp NcoI-BamHI fragment (29 hydrophobic amino acid residues deleted), and fragment C, a 362 bp BamHI-HindIII fragment, as depicted in FIG. 10. A fourth fragment containing the deleted twenty-nine hydrophobic amino acid residues was cloned into the 309 bp NcoI-BamHI fragment as an EcoRV-SnaBI fragment (FIG. 10). The three major subfragments were cloned into pUC vectors, transformed into JM109 cells and their primary nucleotide sequences confirmed, as previously described. The fragments were then gel purified and ligated together to form the 1089 bp full length synthetic HIV-2 TMP. This 1089 bp HindIII fragment was cloned into pUC8 and designated pJC28 (FIG. 11).

Figure 12:
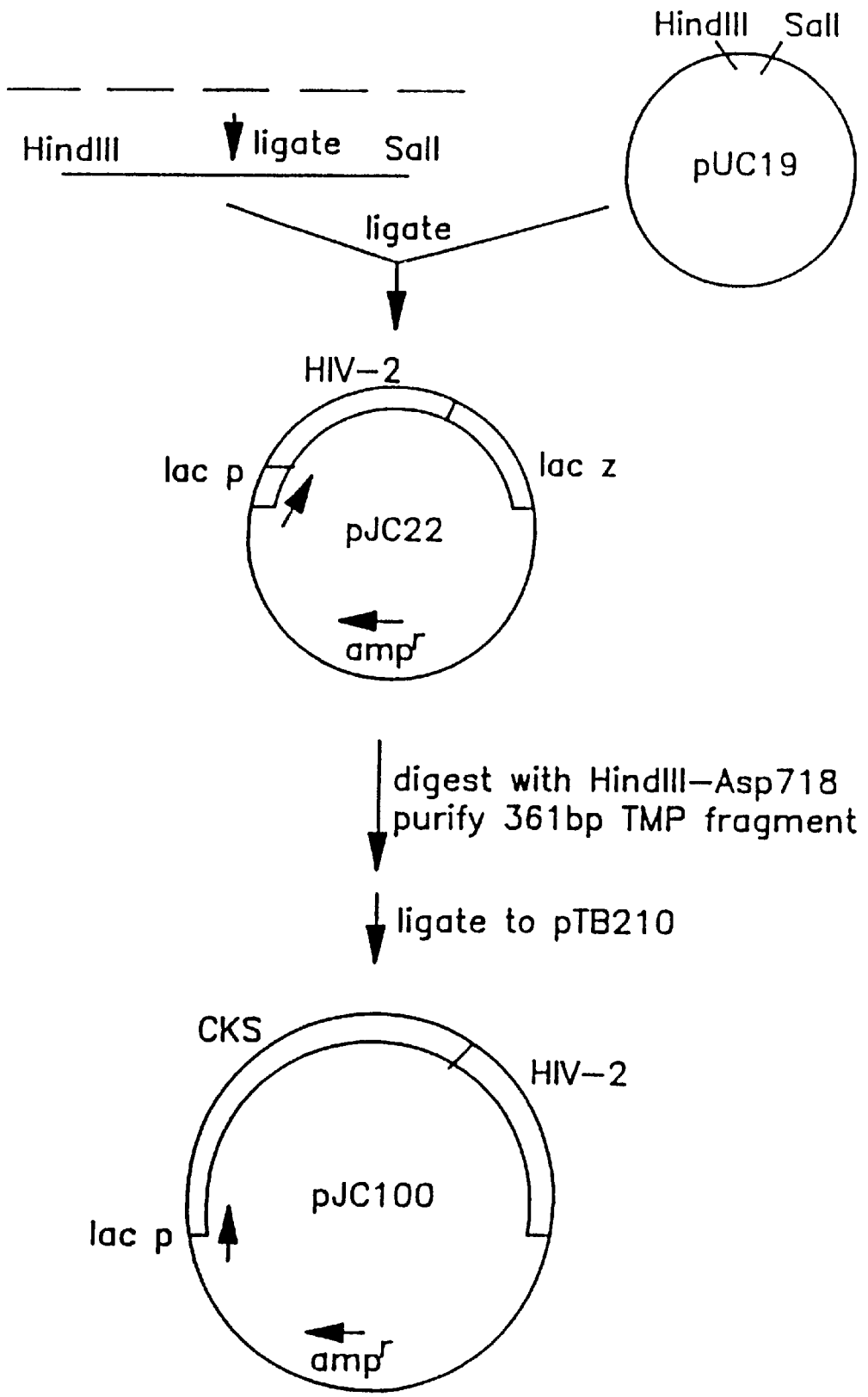
FIG. 12 is a schematic diagram of the cloning of synthetic HIV-2 TMP fragment A into pUC19 to generate pJC22 and into pTB210 to generate pJC100.

Fragment A encoding the amino terminal 108 amino acids of HIV-2 TMP (from Tyr 502 to Trp 609 [Guyader et al., supra]) was cloned at the HindIII-SalI sites of pUC19. A clone, designated pJC22, was identified by restriction mapping and its primary nucleotide sequence was confirmed. Plasmid pJC22 was digested with HindIII-Asp718 to release a 361 bp fragment containing the synthetic HIV-2 TMP gene fragment which was ligated into the HindIII-Asp718 sites of plasmid pTB210 and transformed into *E. coli* XL1 cells. Plasmid pTB210 is disclosed in a U.S. Pat. No. 5,124,255 entitled "CKS Method of Protein Synthesis," to Bolling et al., issued Jun. 23, 1992, which is hereby incorporated by reference. A clone, designated pJC100 (FIG. 12), was isolated and restriction mapped to identify the hybrid gene consisting of CMP-KDO synthetase (CKS) and HIV-2 TMP.

Example 4

Cloning of Synthetic HIV-2 TMP in Lambda pL Vectors

Figure 13:
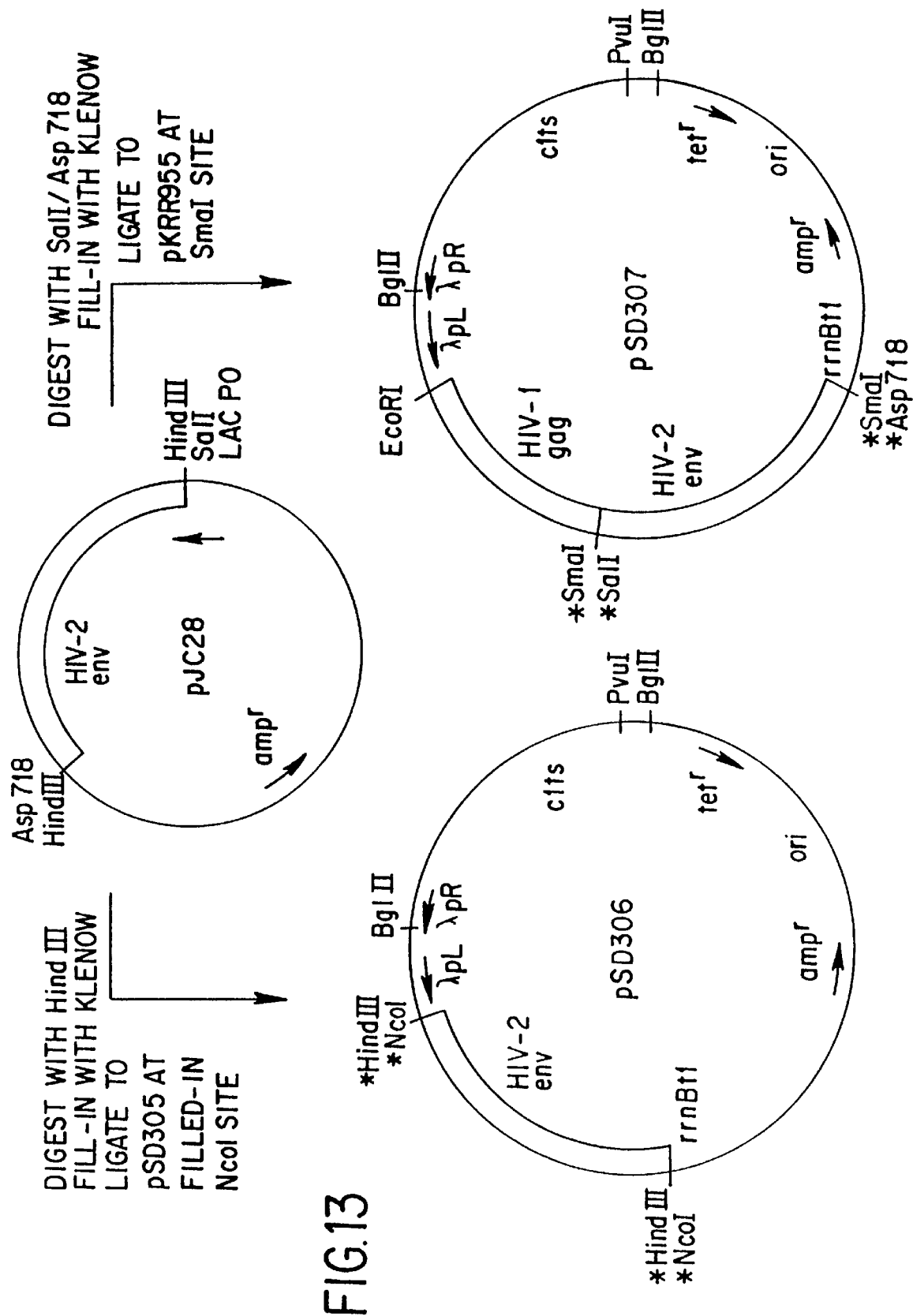
FIG. 13 is a schematic diagram of the cloning of synthetic HIV-2 TMP into lambda pL expression vectors to generate pSD306 and pSD307.

The 1089 bp HindIII fragment containing the entire HIV-2 TMP was isolated from pJC28, filled in with the Klenow fragment of DNA polymerase I to produce blunt ends and cloned directly behind an ATG start codon provided by the filled in NcoI site of pSD305 (pSDKR816 previously described with cits inserted). Similarly, an 1097 bp SalI-Asp718 fragment containing the entire HIV-2 TMP was isolated from pJC28, filled in with the Klenow fragment of DNA polymerase I to produce blunt ends and cloned at the SmaI site of pKRR955 (previously described) to produce an HIV-1 gag/HIV-2 TMP fusion protein. The clone containing the HIV-2 TMP gene under control of the lambda pL promoter was designated pSD306 and the clone containing the HIV-2 TMP as a fusion to HIV-1 gag under control of the lambda pL promoter was designated pSD307, as outlined in FIG. 13. After transformation of pSD306 into *E. coli* CAG456 cells (Baker, PNAS (1984) 81:6779) and pSD307 into *E. coli* pRK248.clts/RR1 cells, single cell clones were isolated and restriction mapped to demonstrate the presence and orientation of the HIV-2 TMP gene. The specific amino acid sequences of pSD306 and pSD307 are presented in FIG. 14, indicating linker derived sequences, HIV-1 gag sequences, and HIV-2 TMP sequences. Expression of the synthetic HIV-2 TMP gene was induced in these cultures by temperature shift methods, as previously described. Aliquots of the cultures before and after induction were subjected to SDS/PAGE analysis for both Coomassie blue staining and immunoblotting using HIV-2 positive human sera, as previously described for the synthetic HIV-1 envelope gene product. Whole cell lysates and the sonicated soluble and insoluble fractions of the cultures were analyzed and are illustrated in FIGS. 15 and 16 for the pSD306 and pSD307 constructs, respectively.

Figure 15A:
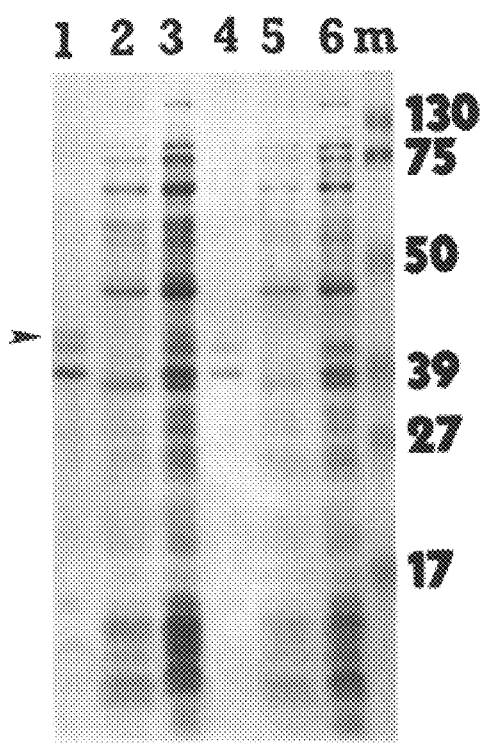
Figure 15B:
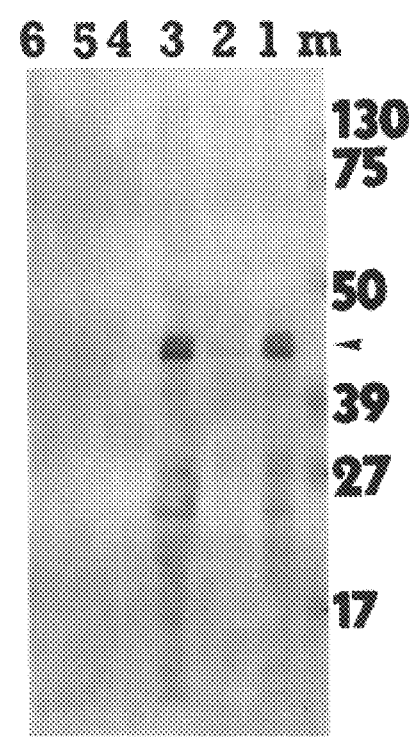

FIGS. 15A and 15B present the expression of pSD306 prior to (T0) and two hours post (T2) induction, analyzed by Coomassie blue staining (FIG. 15A) and immunoblotting (FIG. 15B). Samples were T0 whole cell lysate (lane 1); T0 sonicated soluble fraction (lane 2); T0 sonicated insoluble fraction (lane 3); T2 whole cell lysate (lane 4); T2 sonicated soluble fraction (lane 5); T2 sonicated insoluble fraction (lane 6); and BioRad prestained molecular weight markers (lane M). FIGS. 15A and 15B demonstrate that pSD306 expressed a significant amount of the HIV-2 TMP at time T2, as indicated by the arrows on both the Coomassie stained gel and the immunoblot. This expressed protein is visible in both the whole cell lysate as well as the sonicated insoluble cell fraction of these cultures.

Figure 16A:
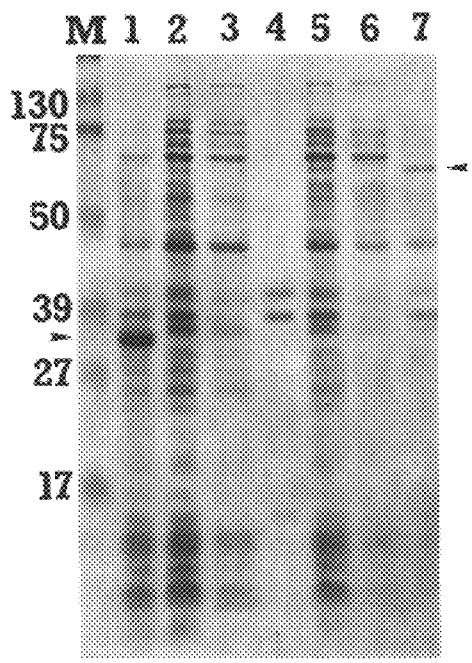
Figure 16B:
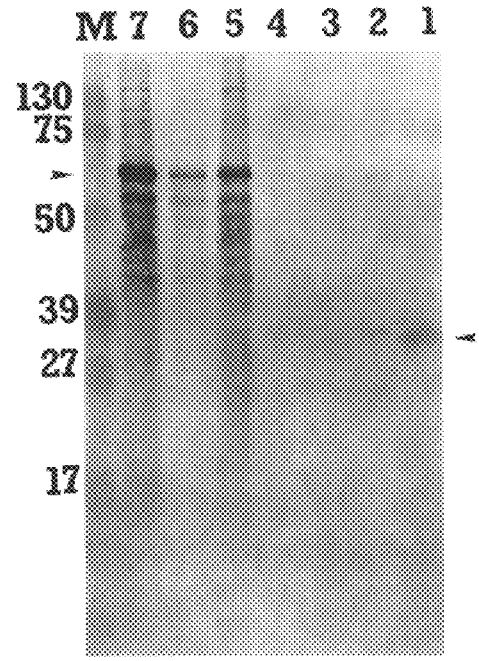

Similarly, FIGS. 16A and 16B present the expression of pSD307 prior to (T0) and two hours post (T2) induction, analyzed by Coomassie blue staining (FIG. 16A) and immunoblotting (FIG. 16B). Samples were pKRR955, T2 whole cell lysate (lane 1); pSD307, T0 whole cell lysate (lane 2), T0 sonicated soluble fraction (lane 3), T0 sonicated insoluble fraction (lane 4), T2 whole cell lysate (lane 5), T2 sonicated soluble fraction (lane 6), T2 sonicated insoluble fraction (lane 7); and BioRad prestained molecular weight markers (lane M). FIGS. 16A and 16B demonstrate that pSD307 expressed a significant amount of the HIV-1 gag/HIV-2 TMP fusion protein at time T2, as indicated by the arrows on both the Coomassie stained gel and the immunoblot. This fusion protein is also visible in both the whole cell lysate and the sonicated insoluble fraction of these cultures. The HIV-1 gag fusion partner (lane 1), although present at higher levels than the HIV-1 gag/HIV-2 TMP fusion protein, showed lower immunoreactivity to HIV-2 specific antibodies.

Example 5

Diagnostic Utility of Synthetic DNA Derived HIV Proteins

The HIV specific proteins overexpressed in *E. coli* were purified using procedures known in the art. The proteins expressed at high levels were immunogenic and were recognized by antibodies produced in HIV-infected individuals (see FIGS. 8, 15 and 16). The HIV specific proteins derived from *E. coli* can be utilized in several immunoassay configurations, as described in CIP application U.S. Ser. No. 020,282, filed Feb. 27, 1987 by Dawson et al., the parent application of which is EPO 86116854.0 (Dec. 4, 1986), as follows with substitution of the antigens of the present invention for the recombinant proteins described therein. For example, a solid support coated with recombinant p24 proteins is contacted with the biological sample and anti-HIV-p24 conjugated to label; unbound sample and unbound anti HIV-p24 are removed from the solid support; and the label is detected to determine the presence of anti-HIV-p24 in the sample. Another detection system comprises coating a solid support with recombinant gp41 proteins; contacting the gp-41 coated solid support with the biological sample and anti-HIV-gp41 conjugated to a label; removing unbound sample and unbound anti-HIV-p41 from the solid support; and detecting the label to determine the presence of anti-HIV-gp41 in the samples. In a modification of the preferred example described hereinbelow, the coated solid support (containing p24 or gp41 or both) is contacted with the biological sample, and then unbound sample is removed. Next, labeled p24 or gp 41 (or both) is added to the solid support. After removal of unbound labeled reagent, any label attached to the solid support is detected to determine presence of HIV antibodies in the sample. In yet another embodiment, the dual detection system comprises a method for detecting antibody to HIV comprising at least two detection systems, one detected system comprising coating a solid support with anti-HIV-p24, contacting the anti-HIV-p24 coated solid support with a biological sample and a recombinant HIV-p24 protein; removing unbound biological sample and recombinant HIV-p24 protein, contacting the anti-HIV-p24 coated solid support with anti-HIV-p24 conjugated to a label, removing unbound labeled anti-HIV-p24 and detecting the label to determine the presence of labeled anti-HIV-p24 bound to the solid support; the other detection system comprising coating a solid support with anti-HIV-gp41, contacting the anti-HIV-gp41 coated solid support with a biological sample and a recombinant HIV-gp41 protein, removing unbound biological sample and recombinant HIV-gp41 protein, contacting the anti-HIV-gp41 coated solid support with anti-HIV-gp41 conjugated to a label; removing unbound labeled anti-HIV-gp41 and detecting the label to determine the presence of labeled anti-HIV-gp41 antibody bound to the solid support. In a preferred configuration, HIV specific proteins were coated on solid support and incubated with test samples. The virus specific antibodies present in the test sample recognized and were bound to the HIV proteins on the solid support. The HIV specific antibodies were quantitated by the use of goat anti-human immunoglobulin conjugated to HRPO.

The HIV-1 exposed individuals were detected by the use of HIV-1 specific proteins, such as HIV-1 gp41 and HIV-1 p24 proteins derived by recombinant DNA techniques, described in the CIP application Serial No. 020,282 thereof, as follows. Using density gradient centrifugation, HIV virus was purified from culture fluids of HIV-infected HT-9 cells supplied by Frederick Cancer Research facility, Frederick, Md. A viral cDNA library was constructed using purified viral RNA extracted from banded virus. Okayama et al., *Mol. and Cell. Biol.,* 3, 280–289 (1983). Labeled viral cDNA fragments were used as probes to screen a cDNA library constructed from poly A selected viral RNA. One clone, pCW11, containing the entire viral 3' LTR plus the 3' open reading frame was used as a probe for subsequent screening of the genomic library resulting in isolation of several clones containing partial or entire viral genome. Using these clones, expression vectors for production of p24 and gp41 in *E. coli* were constructed. One clone, pC23, containing the entire viral gag gene encoded 3 core proteins of about 17 kD (p17), 24 kD (p24) and 15 kD (p15). The most antigenic of the three, p24, was chosen for expression in *E. coli.* The p24 gene fragment was inserted into plasmid, pUC-9 (Pharmacia, Piscataway, N.J.) at a position that would render it under the control of the lac promoter. The resultant plasmid, designated pB1, included DNA encoding for 13 amino acids at the carboxyl terminus of the p17 protein, the entire p24 protein and 59 amino acids of the p15 protein. The protein expressed in *E. coli* matched well with the expected molecular weight and could be readily detected by Western blot analysis. Another clone, p41C, consisting of an 845 bp fragment of the envelope gene, flanked by BglII and Kpn I restriction sites encoded the carboxyl terminus of gp120(45 amino acids) and the entire gp41 protein. Insertion of this gene fragment into pUC-9 and expression of it were performed as in the above-mentioned p24 example. Western blot analysis confirmed the expected molecular weight and antigenicity. Host cells used for propagation of gp41 and p24 were *E. coli* K-12, strain JM103, (lac-pro), sup E, thi, str A, sbc B15, end A, hsd R4/F'tra D 36, pro AB, lac $I^q$ Z M15. Messing et al., *Methods Enzymol.,* 101, 20–78 (1983). Vectors containing the lac Z gene are commercially available (Pharmacia, Piscataway, N.J.). All manipulations involving nucleic acids have been described in Maniatis et al., *Molecular Cloning,* Cold Spring Harbor Laboratory, 3–17 (1982).

The HIV gp41 recombinant protein produced in *E. coli* (clone p41C) was purified using affinity column and ion exchange chromatography. The bacterial lysate supernatant was passed over an affinity column composed of Sepharose 4B beads bound with monoclonal anti-HIV-gp41. The column was washed with a buffer of 0.5% Triton X-100® and the bound HIV gp41 was eluted with the same buffer containing 5 M NaI. The eluted protein solution was dialyzed extensively to remove NaI and mixed 1:1 with an ethanolamine buffer containing 0.1% Tween 20® and 7M urea (Buffer A) and applied to a DEAE anion exchange column. The column was extensively washed in Buffer A, then bound protein was eluted using a 100–500 mM NaCl gradient in Buffer A. Peak fractions of gp41 activity were pooled and dialyzed to remove urea. The p24 recombinant produced in E. coli (clone pB1) was purified by passage of bacterial lysate supernatant over an affinity column composed of Sepharose 4B beads bound with monoclonal anti-HIV-p24. The column was washed with a buffer containing 0.1% Triton X-100®, and the bound p24 was eluted with the same buffer containing 4M guanidine hydrochloride (GuHCl). The eluted protein solution was dialyzed extensively, then reapplied to a second affinity column and eluted as described above. Peak fractions of p24 were pooled and dialyzed to remove GuHCl. To further characterize the recombinant proteins, purified core or envelope antigens were subjected to SDS PAGE and Western blot analysis according to Schupbach et al., *Science,* 224, 503–505 (1984). After electrophoresis of purified envelope protein and staining of gels, specific bands of about 38 and 36 kD were detected along with a few bands of lower molecular weight. These two bands were strongly reactive with human polyclonal and mouse monoclonal antibodies against gp41. Amino terminal sequencing of these two bands demonstrated that both bands contain a portion of the carboxyl terminus of gp120 and a complete gp41 gene product. However, only 70 to 90% of the HIV-2 exposed individuals were detected using these HIV-1 specific proteins, due to cross reactivity between the two strains. The HIV-2 exposed individuals which were not detected using these HIV-1 specific proteins were detected using synthetic DNA derived HIV-2 proteins.

For example, the HIV-2 TMP fragment fused to CKS (pJC100) when supplemented to the recombinant HIV-1 proteins on the solid support described above significantly increased the detection of test samples containing HIV-2 antibodies as illustrated in Table 1, below.

TABLE 1

|  | HIV-1 Test | HIV-1/HIV-2 Test |
| --- | --- | --- |
| Samples Tested* | 127 | 127 |
| Non Reactive | 26 | 0 |
|  | (20.47%) | (0%) |
| Reactive | 101 | 127 |
|  | (79.53%) | (100%) |

*All 127 samples were confirmed positive for the presence of HIV-2 antibodies by western blot analysis using disrupted HIV-2 virus.

Additionally, 3,411 normal blood donors were screened using the HIV-1HIV-2 recombinant assay described above. The recombinant assay demonstrated a specificity of 99.77%, with only eight (0.23%) initial reactive and four (0.12%) repeat reactive samples.

Example 6

Differentiation of HIV-1 and HIV-2 Infections

Frequently, individuals who have been exposed to HIV-2 have antibodies directed against epitopes on HIV-2 proteins which are also present on HIV-1 proteins. Likewise, individuals who have been exposed to HIV-1 have antibodies which cross-react with HIV-2 proteins. Because most of the cross-reactions are related to the gag gene products, the pJP100 protein and a recombinant protein from HIV-1 envelope protein (described in CIP Application Serial Number 020,282 and described herein above) were used to differentiate between individuals infected with HIV-1 and HIV-2.

Two independent enzyme-linked immunoassays were developed. Test 1 used HIV-1 recombinant proteins coated upon a solid phase. Test 2 used HIV-2 TMP (pJP100) coated upon a solid phase. Specimens from HIV seropositive individuals from the United States, Portugal or West Africa were tested for antibodies using these two tests. Endpoint titers were determined by diluting the specimens in normal human plasma and testing the dilutions. As illustrated in Table 2 below, specific tests using synthetic recombinant proteins can be effectively used to differentiate HIV-1 and HIV-2 infections.

TABLE 2

| Specimen | Test 1 Endpoint Titer | Test 2 Endpoint Titer |
| --- | --- | --- |
| Chicago-AIDS-1 | 256 | <1 |
| Chicago-AIDS-2 | 512 | <1 |
| Chicago-AIDS-3 | 512 | <1 |
| Chicago-Asymptomatic-4 | 1024 | <1 |
| Chicago-Asymptomatic-5 | 2048 | <1 |
| Chicago-Asymptomatic-6 | 512 | <1 |
| West Africa-1 | <1 | 2048 |
| West Africa-2 | <1 | 64 |
| Portugal-1 | <1 | 512 |

Biological samples which are easily tested by the methods of the present invention include human and animal body fluids such as whole blood, serum, plasma, urine, saliva, stools, lymphocyte or cell culture preparations and purified and partially purified immunoglobulins. The polypeptides and fragments described herein can be used to determine the presence or absence of antibodies to HIV-1 and HIV-2 antigens by assay methods known to those skilled in the art, and for distinguishing between HIV-1 and HIV-2 infections.

One such assay involves:

a) coating a solid support with the polypeptides and polypeptide fragments disclosed herein;

b) contacting the coated solid support with the biological sample to form an antibody polypeptide complex;

c) removing unbound biological sample from the solid support;

d) contacting the complex on the solid support with a labeled immunoglobulin specific for the antibody; and e) detecting the label to determine the presence or absence of HIV-1 and/or HIV-2 antibodies in the biological sample.

A second assay method involves:

a) coating a solid support with the polypeptides and polypeptide fragments disclosed herein;

b) contacting the coated solid support with the biological sample and the homologous polypeptides conjugated to a label;

c) removing unbound biological sample and unbound labeled polypeptide; and d) detecting the label to determine the presence or absence of HIV-1 and/or HIV-2 antibodies in the biological sample.

Solid supports which can be used in such immunoassays include wells of reaction trays, test tubes, beads, strips, membranes, filters, microparticles or other solid supports which are well known to those skilled in the art. Enzymatic, radioisotopic, fluorescent, chemiluminescent and colloidal particle labels can be used in the aforementioned assays. Furthermore, hapten/labeled anti-hapten systems such as a biotin/labeled anti-biotin system can be utilized in the inventive assays. Both polyclonal and monoclonal antibodies are useful as reagents, and IgG as well as IgM class HIV antibodies may be used as solid support or labeled reagents.

It is evident from the foregoing examples that one skilled in the art could clone together specific subfragments of the synthetic genes constructed to generate new synthetic genes that would have the same characteristics as those illustrated herein. For example, the c-term gp120 subfragment, BS2-10 and subfragment 413-1 can be cloned together to produce synthetic gene products useful as diagnostic and therapeutic reagents for AIDS.

What is claimed is:

1. A method for detecting antibodies to HIV antigens in an individual, which method comprises the steps of:

a) obtaining a sample of a body fluid from the individual;

b) incubating said body fluid with a polypeptide selected from the group consisting of:

(i) an HIV-1 transmembrane protein having the amino acid sequence MGDPMMRDNWRSELYKYKVV-KIEPLGIAPTKAKRRVVQREKRADLAVGILGA-LFLGFLGAAGSTMGARSLTLTVQARQLLSGIV-QQQNNLLRAIKDPKAQQHLLQLTVWGIKQLQ-ARVLAVERYLKDQQLLGIWGCSGKLICTAVP-WNASWSNKSLEDIWNNMTWMQWEREINNY-TNLIYSLLEESQNQQEKNEQELLQLDKWVDA-SLWNWSNITKWLWYIKLFIMIVGGLAGLRIV-FAVLSIVNRVRQGYSPLSFQTRLPNPRGPDRPE-GIDEEGGERDRDRSTRLVDISLALVWEDLRSL-CLFSYHRLRDLLLIATRIVELLGRRGWEVLKY-WWNLLQYVSQELKNSAVSLVNATAIAVAEGT-DRVIEVVWQRAYRAIRHIHRRIRQGLERILLQ-VHASSLESSWQFGPG, and (ii) a fragment of the HIV-2 transmembrane protein having the amino acid sequence YSSAHGRHTRG-VFVLGFLGFLATAGSAMGAASLTVSAQSRTL-LAGIVQQQQQLLDVVKRQQELLRLTVWGTK-NLQARVTAIEKYLQDQARLNSWGCAFRQVC-HTTVPW, for a time and under conditions sufficient to form polypeptide/antibody complexes;

c) incubating said body fluid/polypeptide complexes with a labeled antibody to immunoglobulin, for a time and under conditions sufficient to form polypeptide/antibody/antibody complexes; and d) detecting said label and determining therefrom the presence or absence of antibodies to HIV antigens.

2. A method for detecting antibodies to HIV antigens in an individual, which method comprises the steps of:

a) obtaining a sample of a body fluid from the individual;

b) incubating said body fluid with a solid phase to which has been attached a polypeptide selected from the group consisting of:

(i) an HIV1 transmembrane protein having the amino acid sequence MGDPMMRDNWRSELYKYKVV-KIEPLGIAPTKAKRRVVQREKRADLAVGILGA-LFLGFLGAAGSTMGARSLTLTVQARQLLSGI-VQQQNNLLRAIKDPKAQQHLLQLTVWGIKQ-LQARVLAVERYLKDQQLLGIWGCSGKLICTT-AVPWNASWSNKSLEDIWNNMTWMQWEREI-NNYTNLIYSLLEESQNQQEKNEQELLQLDKW-VDASLWNWSNITKWLWYIKLFIMIVGGLAGL-RIVFAVLSIVNRVRQGYSPLSFQTRLPNPRGPD-RPEGIDEEGGERDRDRSTRLVDISLALVWED-LRSLCLFSYHRLRDLLLIATRIVELLGRRGWE-VLKYWWNLLQYVSQELKNSAVSLVNATAIA-VAEGTDRVIEVVQRAYRAIRHIHRRIRQGLERI-LLQVHASSLESSWQFGPG, and (ii) a fragment of the HIV-2 transmembrane protein having the amino acid sequence YSSAHGRHTR-GVFVLGFLGFLATAGSAMGAASLTVSAQSRT-LLAGIVQQQQQLLDVVKRQQELLRLTVWGT-KNLQARVTAIEKYLQDQARLNSWGCAFRQV-CHTTVPW;

c) incubating said body fluid with a labeled antigen for a time and under conditions sufficient to form polypeptide/antibody/labeled antigen complexes; and d) detecting said label and determining therefrom the presence or absence of antibodies to HIV antigens.

3. The method of claim 2, wherein step b) and step c) are performed simultaneously.

* * * * *

UNITED STATES PATENT AND TRADEMARK OFFICE
CERTIFICATE OF CORRECTION

PATENT NO. : 6,153,377  
DATED : November 28, 2000  
INVENTOR(S) : Sushil G. Devare et al.

Page 1 of 1

It is certified that error appears in the above-identified patent and that said Letters Patent is hereby corrected as shown below:

<u>Column 15,</u>
Line 29, replace "ARVLAVERYLKDQQLLGIWGCSGKLICT" with -- ARVLAVERYLKDQQLLGIWGCSGKLICTT --.
Line 37, replace "DRVIEVVWQRAYRAIHIHRRIRQGLERILLQ" with -- DRVIEWVVQRAYRAIRHIHRRIRQGLERILLQ --.

Signed and Sealed this

Twenty-ninth Day of January, 2002

Attest:

*Attesting Officer*

JAMES E. ROGAN
*Director of the United States Patent and Trademark Office*